(12) United States Patent
Patel et al.

(10) Patent No.: US 9,108,956 B2
(45) Date of Patent: Aug. 18, 2015

(54) CYCLIC ETHER DGAT1 INHIBITORSCYCLIC ETHER DGAT1 INHIBITORS

(71) Applicants: Sejal Patel, Lexington, MA (US); Justin Mao, North Reading, MA (US); Qian Liu, Malden, MA (US); Tyler Harrison, Somerville, MA (US); Rohit Duvadie, Arlington, MA (US); Xin Chen, Lexington, MA (US); Frederic Zecri, Brookline, MA (US)

(72) Inventors: Sejal Patel, Lexington, MA (US); Justin Mao, North Reading, MA (US); Qian Liu, Malden, MA (US); Tyler Harrison, Somerville, MA (US); Rohit Duvadie, Arlington, MA (US); Xin Chen, Lexington, MA (US); Frederic Zecri, Brookline, MA (US)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 14/396,744

(22) PCT Filed: Apr. 26, 2013

(86) PCT No.: PCT/US2013/038350
§ 371 (c)(1),
(2) Date: Oct. 23, 2014

(87) PCT Pub. No.: WO2013/163508
PCT Pub. Date: Oct. 31, 2013

(65) Prior Publication Data
US 2015/0141474 A1 May 21, 2015

Related U.S. Application Data

(60) Provisional application No. 61/639,400, filed on Apr. 27, 2012, provisional application No. 61/790,057, filed on Mar. 15, 2013.

(51) Int. Cl.
*C07D 413/12* (2006.01)
*C07D 417/12* (2006.01)

(52) U.S. Cl.
CPC ............ *C07D 413/12* (2013.01); *C07D 417/12* (2013.01)

(58) Field of Classification Search
CPC .. C07D 417/12; C07D 413/12; A61K 31/429; A61K 31/4245; A61K 31/422; A61K 31/433
See application file for complete search history.

(56) References Cited

FOREIGN PATENT DOCUMENTS

| WO | WO 2007126957 A2 | * | 11/2007 |
|---|---|---|---|
| WO | WO 2012047948 A1 | * | 4/2012 |
| WO | WO 2012051488 A1 | * | 4/2012 |

OTHER PUBLICATIONS

International Preliminary Report on Patentability for International Application No. PCT/US2013/038350, dated Oct. 28, 2014.*
International Search Report for International Application No. PCT/US2013/038350, dated Jun. 21, 2013.*

* cited by examiner

*Primary Examiner* — Matthew Coughlin
(74) *Attorney, Agent, or Firm* — Joshua Roth

(57) ABSTRACT

The invention relates to compounds of formula (I): useful for treating disorders mediated by acyl coA-diacylglycerol acyl transferase 1 (DGAT1), e.g. metabolic disorders. The invention also provides methods of treating such disorders, and compounds and compositions etc. for their treatment.

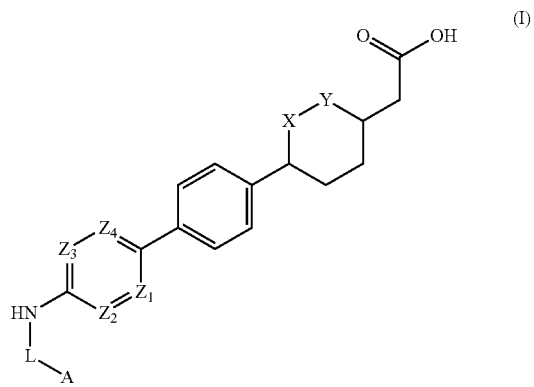

17 Claims, No Drawings

CYCLIC ETHER DGAT1 INHIBITORSCYCLIC ETHER DGAT1 INHIBITORS

RELATED APPLICATIONS

This application claims priority to U.S. Provisional Application No. 61/639,400 filed Apr. 27, 2012 and U.S. Provisional Application No. 61/790,057 filed Mar. 15, 2013, the contents of which are incorporated herein by reference in their entireties.

TECHNICAL FIELD

This invention relates to compounds useful for treating disorders mediated by acyl coA-diacylglycerol acyl transferase 1 (DGAT1), e.g. metabolic disorders. The invention also provides methods of treating such disorders, and compounds and compositions etc. for their treatment.

BACKGROUND ART

Although triglycerides (also known as "triacylglycerides") are essential for normal physiology, excess triglyceride accumulation results in obesity and, particularly when it occurs in nonadipose tissues, is associated with insulin resistance. Obesity increases the risk of many common and serious conditions, including coronary heart disease, hypertension, dyslipidemia, atherosclerosis, type-II diabetes, stroke, osteoarthritis, restrictive pulmonary disease, sleep apnoea, certain types of cancers and inflammatory disorders. The standard treatment for obesity is calorific restriction and increase of physical exercise. However, such approaches are rarely successful and pharmaceutical treatments are required to correct these metabolic disorders.

A potential therapy for these conditions therefore involves inhibiting triglyceride synthesis.

Diacylglycerol acyl-transference (DGAT) is an enzyme that catalyzes the last step in triacylglycerol biosynthesis. DGAT catalyzes the coupling of a 1,2-diacylglycerol with a fatty acyl-CoA resulting in Coenzyme A and triacylglycerol. Two enzymes that display DGAT activity have been identified: DGAT1 (acyl coA-diacylglycerol acyl transferase 1) [Cases et al., *Proc. Natl. Acad. Sci.* 1998, 95:13018-13023] and DGAT2 (acyl coA-diacylglycerol acyl transferase 2) [Cases et al., *J. Biol. Chem.* 2001, 276:38870-38876].

DGAT1 and DGAT2 do not share significant protein sequence homology. Importantly, however, DGAT1 knockout mice are protected from high fat diet-induced weight gain and insulin resistance [Smith et al., *Nature Genetics* 2000, 25:87-90]. The phenotype of the DGAT1 knockout mice suggests that DGAT1 inhibitors would be useful for the treatment of obesity and obesity-associated complications [Smith et al., *Nature Genetics* 2000, 25:87-90].

There is therefore a need for compounds which inhibit the activity of DGAT1.

DISCLOSURE OF THE INVENTION

The inventors have found compounds of formula (I) that are useful for inhibiting the activity of DGAT1.

Accordingly, in a first aspect of the invention, there is provided a compound of formula (I)

In one embodiment, the invention is a compound according to formula (I) or a salt or solvate thereof:

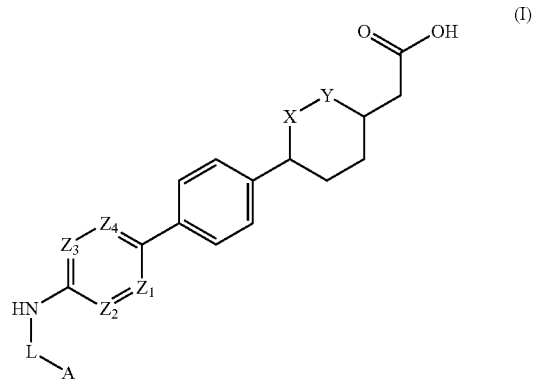

wherein X is O or CH; Y is O or CH; wherein one of X and Y is O and the other is CH; $Z_1$, $Z_2$, $Z_3$ and $Z_4$ are each, independently, N or CH; L is C(O) or absent; and A is a substituted oxazole, thiazole, oxadiazole or thiadiazole substituted with at least one $C_{1-6}$alkyl, $C_{3-7}$cycloalkyl or $C_{1-6}$haloalkyl.

In a second embodiment the compound is of formula (II) or a salt or solvate thereof:

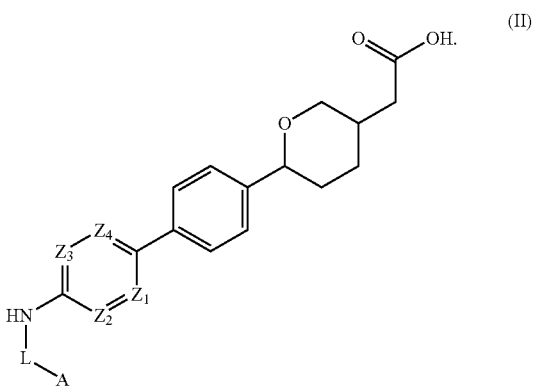

In a third embodiment, the compound is of formula (III) or a salt or solvate thereof:

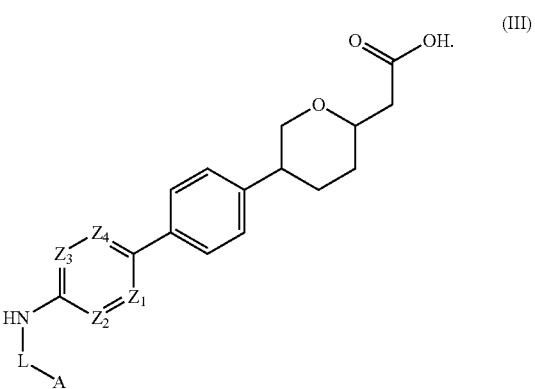

In a fourth embodiment according to the first to third embodiments, the invention is a compound of formula (I), (II) or (III) or a salt or solvate thereof, wherein $Z_1$, $Z_2$, $Z_3$ and $Z_4$ are all CH.

In a fifth embodiment according to the first to third embodiments, the invention is a compound of formula (I), (II) or (III) or a salt or solvate thereof, wherein $Z_1$ is N and $Z_2$, $Z_3$ and $Z_4$ are each CH.

In a sixth embodiment according to the first to third embodiments, the invention is a compound of formula (I), (II) or (III) or a salt or solvate thereof, wherein $Z_2$ is N and $Z_1$, $Z_3$ and $Z_4$ are each CH.

In a seventh embodiment according to the first to third embodiments, the invention is a compound of formula (I), (II) or (III) or a salt or solvate thereof, wherein $Z_1$ and $Z_2$ are both N and $Z_3$ and $Z_4$ are both CH.

In an eighth embodiment according to the first to seventh embodiments, the invention is a compound of formula (I), (II) or (III) or a salt or solvate thereof, wherein L is C(O).

In a ninth embodiment according to the first to seventh embodiments, the invention is a compound of formula (I), (II) or (III) or a salt or solvate thereof, wherein L is absent.

In an tenth embodiment according to the first to ninth embodiments, the invention is a compound of formula (I), (II) or (III) or a salt or solvate thereof, wherein A is selected from:

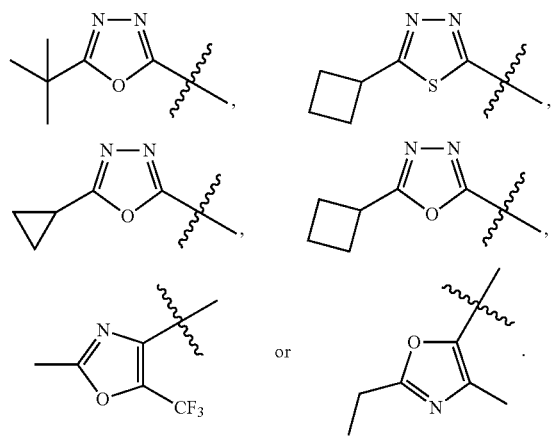

In an eleventh embodiment according to the first to seventh and ninth and tenth embodiments, the invention is a compound according to formula (I), (II) or (III) or a slat or solvate thereof, wherein L is absent and A is selected from:

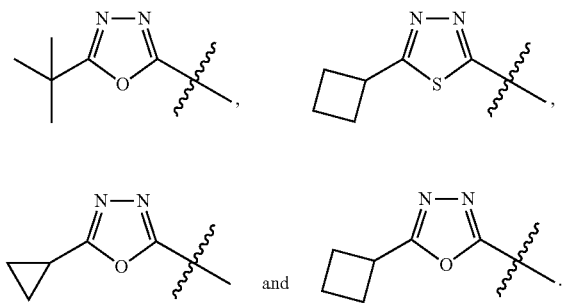

In a twelfth embodiment according to the first to eighth and tenth embodiments, the invention is a compound of formula (I), (II) or (III) or a salt or solvate thereof, wherein L is C(O) and A is

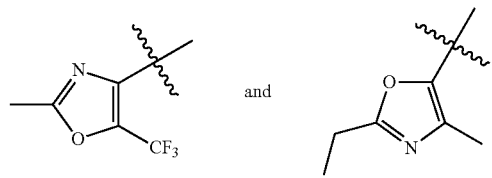

In a thirteenth embodiment according to any one of the first to twelfth embodiments, the invention is a pharmaceutical composition comprising one or more pharmaceutically acceptable carriers and a therapeutically effective amount of a compound according to formula (I), (II) or (III).

In a fourteenth embodiment according to any one of the first to twelfth embodiments, the invention is a combination, in particular a pharmaceutical combination, comprising a therapeutically effective amount of the compound according to formula (I), (II) and (III) and a second therapeutically active agent.

In a fifteenth embodiment according to any one of the first to twelfth embodiments, the invention is a method for the treatment of a disease or condition mediated by DGAT1 activity in a subject, wherein the method comprises administering to the subject a therapeutically effective amount of the compound according to formula (I), (II) and (III).

In a sixteenth embodiment according to any one of the first to twelfth and fifteenth embodiments, the disease or condition is selected from the group consisting of HCV, impaired glucose tolerance, Type II diabetes or obesity.

In a seventeenth embodiment according to any one of the first to twelfth embodiments, the invention is a method of treating HCV, impaired glucose tolerance, Type II diabetes or obesity comprising administering to a subject in need thereof an effective amount of a composition comprising a compound of to formula (I), (II) and (III).

In an eighteenth embodiment according to any one of the first to twelfth embodiments, the invention is a compound according to formula (I), (II) and (III), for use as a medicament.

In a nineteenth embodiment according to any one of the first to twelfth embodiments, the invention is the use of a compound according to formula (I), (II) and (III), in the manufacture of a medicament for the treatment of a disease or condition mediated by DGAT1 activity.

In a twentieth embodiment according to any one of the first to twelfth embodiments, the invention is the use of a compound to formula (I), (II) and (III), for the treatment of HCV, impaired glucose tolerance, Type II diabetes or obesity.

In a twentyfirst embodiment according to any one of the first to twelfth embodiments, the invention is a method for the prevention, delay of progression or treatment of a disease exacerbated by inadequate phosphatidylcholine production, comprising: administering to a warm-blooded animal in need thereof a therapeutically effective amount of a DGAT1 inhibitor of formula (I), (II) or (III). In an exemplary embodiment, the warm-blooded animal is a human.

In a twentysecond embodiment according to any one of the first to twelfth embodiments, the invention is use of a DGAT1 inhibitor of formula (I), (II) or (III) for the preparation of a pharmaceutical composition for the treatment of a disorder or disease exacerbated by inadequate phosphatidylcholine production in a subject mediated by the inhibition of DGAT1.

In a twentythird embodiment according to any one of the first to twelfth embodiments, the invention is a DGAT1 inhibitor of formula (I), (II), (III), or a pharmaceutically acceptable salt or ester thereof; for use in the prevention, delay of progression or treatment of a disease or condition which is selected from chylomicronemia 5 syndrome, familial chylomicronemia syndrome, and Type V hyperlipoproteinemia.

In a twentyfourth embodiment according to any one of the first to twelfth embodiments, the invention is a DGAT1 inhibitor of formula (I), (II) or (III), or a pharmaceutically acceptable salt or ester thereof, for use in the reduction of postprandial triglyceride levels in patients suffering from a disease or condition which is selected from chylomicronemia syndrome, familial chylomicronemia syndrome, and Type V hyperlipoproteinemia.

In a twentyfifth embodiment according to any one of the first to twelfth embodiments, the invention is a DGAT1 inhibitor of formula (I), (II) or (III), or a pharmaceutically acceptable salt or ester thereof, for use in the prevention, delay of progression or treatment of pancreatitis in patients suffering from a disease or condition which is selected from chylomicronemia syndrome, familial chylomicronemia syndrome, and Type V hyperlipoproteinemia.

In a twentysixth embodiment according to any one of the first to twelfth embodiments, the invention is a DGAT1 inhibitor of formula (I), (II) or (III), or a pharmaceutically acceptable salt or ester thereof, for use in the prevention, delay of progression or treatment of a symptom selected from recurrent episodes of pancreatitis, deposition of triglycerides in the skin in the form of eruptive xanthomas, hepatosplenomegaly, milky white triglyceride in the blood vessels in the back of the eye (lipemia retinalis), and mild neuro-cognitive deficits.

In a twentyseventh embodiment according to the first embodiment, the invention is a compound selected from at least one of:
2-(5-(4'-(2-methyl-5-(trifluoromethyl)oxazole-4-carboxamido)-[1,1'-biphenyl]-4-yl)tetrahydro-2H-pyran-2-yl)acetic acid;
2-(5-(4'-(2-methyl-5-(trifluoromethyl)oxazole-4-carboxamido)-[1,1'-biphenyl]-4-yl)tetrahydro-2H-pyran-2-yl)acetic acid, cis enantiomer 1;
2-(5-(4'-(2-methyl-5-(trifluoromethyl)oxazole-4-carboxamido)-[1,1'-biphenyl]-4-yl)tetrahydro-2H-pyran-2-yl)acetic acid, trans enantiomer 1;
2-(5-(4'-(2-methyl-5-(trifluoromethyl)oxazole-4-carboxamido)-[1,1'-biphenyl]-4-yl)tetrahydro-2H-pyran-2-yl)acetic acid, trans enantiomer 2;
2-(5-(4'-(2-methyl-5-(trifluoromethyl)oxazole-4-carboxamido)-[1,1'-biphenyl]-4-yl)tetrahydro-2H-pyran-2-yl)acetic acid, cis enantiomer 2;
2-(5-(4'-((5-cyclobutyl-1,3,4-oxadiazol-2-yl)amino)-[1,1'-biphenyl]-4-yl)tetrahydro-2H-pyran-2-yl)acetic acid, racemate;
2-(6-(4'-((5-cyclobutyl-1,3,4-oxadiazol-2-yl)amino)-[1,1'-biphenyl]-4-yl)tetrahydro-2H-pyran-3-yl)acetic acid sodium salt, racemate;
2-(6-(4'-((5-cyclobutyl-1,3,4-oxadiazol-2-yl)amino)-[1,1'-biphenyl]-4-yl)tetrahydro-2H-pyran-3-yl)acetic acid sodium salt, cis enantiomer 1;
2-(6-(4'-((5-cyclobutyl-1,3,4-oxadiazol-2-yl)amino)-[1,1'-biphenyl]-4-yl)tetrahydro-2H-pyran-3-yl)acetic acid sodium salt, trans enantiomer 1;
2-(6-(4'-((5-cyclobutyl-1,3,4-oxadiazol-2-yl)amino)-[1,1'-biphenyl]-4-yl)tetrahydro-2H-pyran-3-yl)acetic acid sodium salt, cis enantiomer 2;
2-(6-(4'-((5-cyclobutyl-1,3,4-oxadiazol-2-yl)amino)-[1,1'-biphenyl]-4-yl)tetrahydro-2H-pyran-3-yl)acetic acid sodium salt, trans enantiomer 2; and a slat or solvate thereof.

Compounds of Formula (I)-(III) etc. and Derivatives Thereof

As used herein, the terms "compounds of the invention" and "compound of formula (I)" etc. include pharmaceutically acceptable derivatives thereof and polymorphs, isomers and isotopically labelled variants thereof. Furthermore, the term "compounds of the invention" and "compound of formula (I)" etc include compounds of formula (II) and (III), and the embodiments thereof disclosed herein.

Pharmaceutically Acceptable Derivatives

The term "pharmaceutically acceptable derivative" includes any pharmaceutically acceptable salt, solvate, hydrate or prodrug of a compound of formula (I). In one embodiment, the pharmaceutically acceptable derivatives are pharmaceutically acceptable salts, solvates or hydrates of a compound of formula (I).

Pharmaceutically Acceptable Salts

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Solvates & Hydrates

The compounds of the invention may exist in both unsolvated and solvated forms. The term "solvate" includes molecular complexes comprising a compound of the invention and one or more pharmaceutically acceptable solvent molecules such as water or $C_{1-6}$ alcohols, e.g. ethanol. The term "hydrate" means a "solvate" where the solvent is water.

Prodrugs

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

Description of Isomeric Forms and Separation Methods

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Amorphous & Crystalline Forms

The compounds of the invention may exist in solid states from amorphous through to crystalline forms. All such solid forms are included within the invention.

Isomeric Forms

As used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate.

"Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Isotopic Labeling

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2$H, $^3$H, $^{11}$C, $^{13}$C, $^{14}$C, $^{15}$N, $^{18}$F $^{31}$P, $^{32}$P, $^{35}$S, $^{36}$Cl, $^{125}$I respectively. The invention includes various isotopically labeled compounds as defined herein, for example those into which radioactive isotopes, such as $^3$H and $^{14}$C, or those into which non-radioactive isotopes, such as $^2$H and $^{13}$C are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Co-Crystals

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

Treatment of Diseases and Conditions

Compounds of formula (I) have been found to be inhibitors of DGAT1.

The invention provides a compound of formula (I) for use in therapy. The invention further provides a pharmaceutical composition comprising a compound of formula (I) in combination with a pharmaceutically acceptable excipient.

The invention further provides a method for the treatment of a disease or condition mediated by DGAT1, comprising the step of administering a therapeutically effective amount of a compound of formula (I) to a patient. The invention also provides the use of a compound of formula (I) in the manufacture of a medicament for the treatment of a disease or condition mediated by DGAT1. The invention also provides a compound of formula (I) for use in treating a disease or condition mediated by DGAT1.

The invention also provides a crystal of DGAT1 and a compound of formula (I). Such crystals can be used for X-ray diffraction studies of DGAT1 inhibition, e.g. to provide atomic structural information in order to aid rational design of further DGAT1 inhibitors.

The DGAT1 inhibitory activity of the compounds of the invention may be demonstrated by the DGAT1 assay disclosed herein (see "DGAT1 Inhibition Assay"). Preferred compounds of the invention have an $IC_{50}$ in the DGAT1 Inhibition Assay of <100 µM, in one embodiment <10 µM, in another embodiment <1 µM, in another embodiment <100 nM, and in another embodiment <10 nM.

Diseases and Conditions Mediated by DGAT1

The invention is useful for the treatment of a disease or condition mediated by DGAT1. Diseases and conditions mediated by DGAT1 include: metabolic disorders such as obesity, diabetes (e.g. Type II diabetes), anorexia nervosa, bulimia, cachexia, syndrome X, insulin resistance, glucose tolerance, hypoglycemia, hyperglycemia, hyperuricemia, hyperinsulinemia, hypercholesterolemia, hyperlipidemia, dyslipidemia, mixed dyslipidemia, hypertriglyceridemia, pancreatitis, and nonalcoholic fatty liver disease; cardiovascular diseases, such as atherosclerosis, arteriosclerosis, acute heart failure, congestive heart failure, coronary artery disease, cardiomyopathy, myocardial infarction, angina pectoris, hypertension, hypotension, stroke, ischemia, myocardial ischemia, ischemic reperfusion injury, aneurysm, restenosis, and vascular stenosis; neoplastic diseases, such as solid tumors, skin cancer, melanoma, lymphoma, and endothelial cancers, for example, breast cancer, lung cancer, colorectal cancer, stomach cancer, other cancers of the gastrointestinal tract (e.g. esophageal cancer and pancreatic cancer), prostate cancer, kidney cancer, liver cancer, bladder cancer, cervical cancer, uterine cancer, testicular cancer, and ovarian cancer; dermatological conditions, such as acne vulgaris; hepatitis C virus (HCV); pathogens that target lipid droplets (e.g. dengue and *chlamydia*); and infectious agents which require lipid droplets and/or triglycerides in their lifecycle.

One embodiment, the disease or condition mediated by DGAT 1 is impaired glucose tolerance (IGT), Type II diabetes or obesity.

As used herein a patient is suffering from "obesity" if the patient exhibits at least one of:
- a body mass index (BMI), i.e. the patient's mass (in kg) divided by the square of the patient's height (in m), of 30 or more;
- an absolute waist circumference of >102 cm in men or >88 cm in women;
- a waist-to-hip ratio >0.9 in men or >0.85 in women; or
- a percent body fat >25% in men or >30% in women.

As used herein a patient is suffering from "Type II diabetes" if they meet the World Health Organization criteria for Diabetes diagnosis (Definition and diagnosis of diabetes mellitus and intermediate hyperglycemia, WHO, 2006), i.e. the patient exhibits at least one of:
- a fasting plasma glucose ≥7.0 mmol/l (126 mg/dl); or
- a venous plasma glucose ≥11.1 mmol/l (200 mg/dl) 2 hours after ingestion of 75 g oral glucose load.

As used herein a patient is suffering from "IGT" if they meet the World Health Organization criteria for IGT diagnosis (Definition and diagnosis of diabetes mellitus and intermediate hyperglycemia, WHO, 2006), i.e. the patient exhibits both of:

a fasting plasma glucose <7.0 mmol/l (126 mg/dl); and
a venous plasma glucose ≥7.8 and <11.1 mmol/l (200 mg/dl) 2 hours after ingestion of 75 g oral glucose load.

In yet another aspect, the invention is useful as an anorectic.

In one embodiment, the disease or condition mediated by DGAT 1 is HCV (Harris C, Hemandez C, Carpentier A, Kaehlcke K, Rosenberg A R, Farese R V Jr, Ott M Efficient hepatitis C virus particle formation requires diacylglycerol acyltransferase-1. Herker E, Nat Med. 2010 November; 16(11):1295-8. & Charles Harris, Eva Herker, Robert V. Farese Jr., Melanie Ott, The Journal of Biological Chemistry, 286, 42615-42625.)

In another embodiment, the disease or condition mediated by DGAT1 is myocardial ischemia Stanley, W. C., Expert opinion in Investig. Drugs; 11(5): 615-629, 2002; and Dyck, J. R. and Lopaschuk, G. D., J. Mol. Cell. Cardiol. 34(9): 1099-1109, 2002].

In one embodiment, increasing cellular phosphatidyl choline is achieved by DGAT1 inhibition and used as an approach to the therapeutic increase of phosphatidylcholine in plasma lipoproteins and intestinal epithelium (Kent C, Biochim. Biophys. Acta, 1733: 53-66, 2005; Coleman R A, Prog. Lipid Res., 34: 134-176, 2004; Goni F M, et al. Prog. Lipid Res. 38: 1-48, 1999; Jenkins G M, et al., Cell. Mol. Life Sci. 62: 2305-2316, 2005; Becker K P, et al. Cell Mol. Life Sci. 62: 1448-1461, 2005; Kruit J K, et al., World J. Gastroenterol., 12: 6429-6439, 2006; Lewis G F, Curr. Opin. Cardiol., 21: 345-352, 2006; Ehehalt R, Scand. J. of Gastroenterology, 39: 737-742; Stremmel W, Gut, 54: 966-971, 2005; Treede I, J. Biol. Chem., 282: 27155-27164, 2007; Cases et al, Proc. Natl. Acad. Sci. 95:13018-13023, 1998; Cases et al, J. Biol. Chem. 276:38870-38876, 2001; and Smith et al, Nature Genetics 25:87-90, 2000).

In another embodiment, the present invention relates to the use of a DGAT1 inhibitor, or a pharmaceutically acceptable salt or ester thereof, for the treatment of, or the prevention, delay of progression, or treatment of a disease or condition which is selected from chylomicronemia syndrome, familial chylomicronemia syndrome and Type V hyperlipoproteinemia. The present invention further relates to the use of a pharmaceutical composition comprising a DGAT1 inhibitor, or a pharmaceutically acceptable salt or ester thereof, for the prevention, delay of progression, or treatment of a disease or condition which is selected from chylomicronemia syndrome, familial chylomicronemia syndrome and Type V hyperlipoproteinemia.

Hyperlipidemia, or the presence of elevated levels of lipids in the bloodstream, can take the form of hypercholesterolemia (elevated cholesterol), hypertriglyceridemia (elevated triglyceride) or a combination of the two. Hypercholesterolemia, which can further be subdivided, is typically associated with increased risk of atherosclerosis cardiovascular disease. Hypertriglyceridemia occurs when the body's production or intake of triglyceride exceeds the body's ability to metabolize or remove the triglyceride from the bloodstream. The most severe form of hypertriglyceridemia is chylomicronemia (also called hyperchylomicronemia), and is associated with an increased risk of pancreatitis. Chylomicrons are lipoprotein particles that carry absorbed dietary fat from the gut to other body tissues via the bloodstream, and are typically present only during meal times. Chylomicronemia is defined as having the presence of chylomicrons in the bloodstream during times of fasting, and is typically associated with total plasma triglyceride levels above 1000 mg/dL.

The chylomicronemia syndrome refers to a set of clinical complications associated with high chylomicron levels. Typically, patients with the chylomicronemia syndrome have markedly elevated fasting triglyceride levels (1000-2000 mg/dL) with profound excursions (up to 5000 mg/dL and higher) following oral fat intake. The massively elevated plasma triglyceride levels are associated with a number of clinical findings and complications including recurrent episodes of pancreatitis, deposition of triglycerides in the skin in the form of eruptive xanthomas, epatosplenomegaly, a milky pink appearance of the blood vessels in the back of the eye (lipemia retinalis), and mild neuro-cognitive deficits.

The chylomicronemia syndrome can be further subdivided into two groups based on ultracentrifugation of lipoprotein species (see "A system for phenotyping hyperlipoproteinemia", Fredrickson D. S., Lees R. S. Circulation, 1965 March; 31, pp. 321-327).

Fredrickson classification Type I, also known as the familial chylomicronemia syndrome (FCS), patients have accumulation of only chylomicrons in the bloodstream whereas Fredrickson classification Type V, also known as Type V hyperlipoproteinemia, patients have accumulation of both chylomicrons and very low density lipoproteins (VLDL) in the bloodstream.

The familial chylomicronemia syndrome (FCS or Type I hyperlipoproteinemia) is caused by a homozygous or compound heterozygous defect in the clearance of chylomicrons from the bloodstream. The most common cause of FCS is a defect in lipoprotein lipase (LPL), the protein that hydrolyzes triglycerides carried on chylomicrons. Other causes of FCS include defects in apolipoprotein CII (apoCII, a co-activator of LPL) or glycosylphosphatidylinositol-anchored high-density lipoprotein-binding protein 1 (GPIHBP1, an anchoring protein of LPL).

Type I patients are usually identified by early onset as youth of hypertriglyceridemia and pancreatitis. Thus, patients with FCS typically present in childhood with massively elevated triglyceride levels (>2,000 mg/dL), and recurrent bouts of abdominal pain due to pancreatitis. Into adulthood, the triglyceride levels remain elevated, and patients typically experience multiple episodes of abdominal pain and pancreatitis, which can result in hospitalization and death.

Patients also experience other manifestations including eruptive xanthomas, lipemia retinalis, hepatosplenomegaly, and mild neuro-cognitive deficits. The main therapeutic goal in FCS treatment is to prevent or treat pancreatitis via the reduction of triglycerides. Unfortunately, standard lipid-lowering therapies, such as fibrates, omega-3 fatty acids, statins and nicotinic acid derivatives (niacin), are not effective in lowering triglycerides in patients with FCS. Therefore, the standard of care therapy for FCS patients is a very low fat diet (≤10% by calories), something which is very difficult to stay compliant with throughout a lifetime [The Familial Chylomicronemia Syndrome. Santamarina-Fojo S. Lipid Disorders 1998. 27(3): 551-567].

Another approach to treat FCS that is under investigation is gene therapy using a replication-deficient Adeno-Associated Viral vector to deliver a naturally-occurring, "beneficial" variant of LPL (Glybera@) intramuscularly. However this treatment is only transiently effective and requires immunosuppression with mycophenolate, cyclosporine, and steroids [Alipogene tiparvovec, and adeno-associated virus encoding the Ser(447)X variant of human lipoprotein lipase gene for the treatment of patients with lipoprotein lipase deficiency. Burnett J R., Hooper A J. Curr Opin Mol Ther 2009. 6:681-691].

At present there is thus no effective pharmacotherapy for treating FCS and there is thus a need for new methods of treating familial chylomicronemia syndrome (FCS), also known as Type I hyperlipoproteinemia.

Type V hyperlipoproteinemia patients represent a second group at risk for the chylomicronemia syndrome and are usually diagnosed by severe hypertriglyceridemia as adults. This is a heterogeneous group at the extreme end of a spectrum of multifactorial hypertriglyceridemia. Patients with Type V hyperlipoproteinemia generally have both an underlying genetic cause and one or more acquired causes of hypertriglyceridemia. The underlying genetic causes include well characterized dyslipidemia such as familial combined hyperlipidemia (Type IIA), dysbetalipoproteinemia (Type III) and familial hypertriglyceridemia (Type VI), and a group of less well characterized dyslipidemias (e.g. heterozygous LPL deficiency, defects in apoA & apoC genes, defects in fatty acid binding and transport proteins).

Acquired causes of hypertriglyceridemia include comorbid diseases (e.g. type 2 diabetes, obesity, insulin resistance, lipodystrophy, hypothyroidism), medications (e.g. beta blockers, thiazide diuretics, estrogen, glucocorticoids, transplant medications), and other factors (e.g. pregnancy, alcohol intake).

The primary goal of therapy in Type V patients is to reduce the triglyceride levels, and therefore reduce the risk of pancreatitis. Most patients can be successfully treated by addressing the underlying acquired cause(s) of the elevated triglycerides, such as reducing the amount of dietary fat intake, treating uncontrolled co-morbid diseases such as T2DM (Type 2 diabetes mellitus), discontinuing offending medications, and initiating lipid lowering medications such as fibrates, omega-3 fatty acids, or nicotinic acid derivatives (niacin) [Chylomicronemia Syndrome. Chait A., Brunzell J. Adv Intem Med 5 1992. 37:249-73.].

Despite optimal therapy, some Type V patients continue to have elevated triglyceride levels. There is thus a need for new methods of treating Type V hyperlipoproteinemia.

Therapeutic Definitions

As used herein, "treatment" includes curative and prophylactic treatment. As used herein, a "patient" means an animal, preferably a mammal, preferably a human, in need of treatment.

The amount of the compound of the invention administered should be a therapeutically effective amount where the compound or derivative is used for the treatment of a disease or condition and a prophylactically effective amount where the compound or derivative is used for the prevention of a disease or condition.

The term "therapeutically effective amount" used herein refers to the amount of compound needed to treat or ameliorate a targeted disease or condition. The term "prophylactically effective amount" used herein refers to the amount of compound needed to prevent a targeted disease or condition. The exact dosage will generally be dependent on the patients status at the time of administration. Factors that may be taken into consideration when determining dosage include the severity of the disease state in the patient, the general health of the patient, the age, weight, gender, diet, time, frequency and route of administration, drug combinations, reaction sensitivities and the patients tolerance or response to therapy. The precise amount can be determined by routine experimentation, but may ultimately lie with the judgement of the clinician. Generally, an effective dose will be from 0.01 mg/kg/day (mass of drug compared to mass of patient) to 1000 mg/kg/day, e.g. 1 mg/kg/day to 100 mg/kg/day. Compositions may be administered individually to a patient or may be administered in combination with other agents, drugs or hormones.

Administration & Formulation

General

For pharmaceutical use, the compounds of the invention may be administered as a medicament by enteral or parenteral routes, including intravenous, intramuscular, subcutaneous, transdermal, airway (aerosol), oral, intranasal, rectal, vaginal and topical (including buccal and sublingual) administration. The compounds of formula (I) should be assessed for their biopharmaceutical properties, such as solubility and solution stability (across pH), permeability, etc., in order to select the most appropriate dosage form and route of administration for treatment of the proposed indication.

The compounds of the invention may be administered as crystalline or amorphous products. The compounds of the invention may be administered alone or in combination with one or more other compounds of the invention or in combination with one or more other drugs (or as any combination thereof). Generally, they will be administered as a formulation in association with one or more pharmaceutically acceptable excipients. The term "excipient" includes any ingredient other than the compound(s) of the invention which may impart either a functional (e.g drug release rate controlling) and/or a non-functional (e.g. processing aid or diluent) characteristic to the formulations. The choice of excipient will to a large extent depend on factors such as the particular mode of administration, the effect of the excipient on solubility and stability, and the nature of the dosage form.

Typical pharmaceutically acceptable excipients include:
diluents, e.g. lactose, dextrose, sucrose, mannitol, sorbitol, cellulose and/or glycine;
lubricants, e.g. silica, talcum, stearic acid, its magnesium or calcium salt and/or polyethyleneglycol;
binders, e.g. magnesium aluminum silicate, starch paste, gelatin, tragacanth, methylcellulose, sodium carboxymethylcellulose and/or polyvinylpyrrolidone;
disintegrants, e.g. starches, agar, alginic acid or its sodium salt, or effervescent mixtures; and/or
absorbants, colorants, flavors and/or sweeteners.

A thorough discussion of pharmaceutically acceptable excipients is available in Gennaro, Remington: The Science and Practice of Pharmacy 2000, 20th edition (ISBN: 0683306472).

Accordingly, in one embodiment, the present invention provides a pharmaceutical composition comprising a compound of formula (I) and a pharmaceutically acceptable excipient.

General Galenic Aspects

In another aspect, the present invention provides a pharmaceutical composition comprising a compound of the present invention, or a pharmaceutically acceptable salt thereof, and a pharmaceutically acceptable carrier. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers, etc.

Typically, the pharmaceutical compositions are tablets or gelatin capsules comprising the active ingredient together with a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and/or
e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient. Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

Dosage Forms

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The activity of a compound according to the present invention can be assessed by the following in vitro & in vivo methods.

Combination Therapy

The compound of formula (I) may be administered alone, or may be administered in combination with another therapeutic agent (i.e. a different agent to the compound of formula (I)). Preferably, the compound of the invention and the other therapeutic agent are administered in a therapeutically effective amount.

The compound of the present invention may be administered either simultaneously with, or before or after, the other therapeutic agent. The compound of the present invention may be administered separately, by the same or different route of administration, or together in the same pharmaceutical composition.

In one embodiment, the invention provides a product comprising a compound of formula (I) and another therapeutic agent as a combined preparation for simultaneous, separate or sequential use in therapy. In one embodiment, the therapy is the treatment of a disease or condition mediated by DGAT1. Products provided as a combined preparation include a composition comprising the compound of formula (I) and the other therapeutic agent together in the same pharmaceutical composition, or the compound of formula (I) and the other therapeutic agent in separate form, e.g. in the form of a kit.

In one embodiment, the invention provides a pharmaceutical composition comprising a compound of formula (I) and another therapeutic agent. Optionally, the pharmaceutical composition may comprise a pharmaceutically acceptable excipient, as described above in "Administration & Formulation".

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I) in the manufacture of a medicament for treating a disease or condition mediated by DGAT1, wherein the medicament is prepared for administration with another therapeutic agent. The invention also provides the use of a another therapeutic agent in the manufacture of medicament for treating a disease or condition mediated by DGAT1, wherein the medicament is prepared for administration with a compound of formula (I).

The invention also provides a compound of formula (I) for use in a method of treating a disease or condition mediated by DGAT1, wherein the compound of formula (I) is prepared for administration with another therapeutic agent. The invention also provides another therapeutic agent for use in a method of treating a disease or condition mediated by DGAT1, wherein the other therapeutic agent is prepared for administration with a compound of formula (I). The invention also provides a compound of formula (I) for use in a method of treating a disease or condition mediated by DGAT1, wherein the compound of formula (I) is administered with another therapeutic agent. The invention also provides another therapeutic agent for use in a method of treating a disease or condition mediated by DGAT1, wherein the other therapeutic agent is administered with a compound of formula (I).

The invention also provides the use of a compound of formula (I) in the manufacture of a medicament for treating a disease or condition mediated by DGAT1, wherein the patient has previously (e.g. within 24 hours) been treated with another therapeutic agent. The invention also provides the use of another therapeutic agent in the manufacture of a medicament for treating a disease or condition mediated by DGAT1, wherein the patient has previously (e.g. within 24 hours) been treated with a compound of formula (I).

In one embodiment, the other therapeutic agent is selected from:
antidiabetic agents, such as insulin, insulin derivatives and mimetics; insulin secretagogues such as the sulfonylureas, e.g. Glipizide, glyburide and Amaryl; insulinotropic sulfonylurea receptor ligands such as meglitinides, e.g. nateglinide and repaglinide; protein tyrosine phosphatase-1B (PTP-1B) inhibitors such as PTP-112; Cholesteryl ester transfer protein (CETP) inhibitors such as torcetrapib, GSK3 (glycogen synthase kinase-3) inhibitors such as SB-517955, SB-4195052, SB-216763, NN-57-05441 and NN-57-05445; RXR ligands such as GW-0791 and AGN-194204; sodium-dependent glucose cotransporter inhibitors such as T-1095; glycogen phosphorylase A inhibitors such as BAY R3401; biguanides such as metformin; alpha-glucosidase inhibitors such as acarbose; GLP-1 (glucagon like peptide-1), GLP-1 analogs such as Exendin-4 and GLP-1 mimetics; and DPPIV (dipeptidyl peptidase IV) inhibitors such as vildagliptin;

hypolipidemic agents such as 3-hydroxy-3-methyl-glutaryl coenzyme A (HMG-CoA) reductase inhibitors, e.g. lovastatin, pitavastatin, simvastatin, pravastatin, cerivastatin, mevastatin, velostatin, fluvastatin, dalvastatin, atorvastatin, rosuvastatin and rivastatin; squalene synthase inhibitors; FXR (famesoid X receptor) and LXR (liver X receptor) ligands; cholestyramine; fibrates; nicotinic acid and aspirin;

anti-obesity agents such as orlistat or rimonabant;

anti-hypertensive agents, e.g. loop diuretics such as ethacrynic acid, furosemide and torsemide; angiotensin converting enzyme (ACE) inhibitors such as benazepril, captopril, enalapril, fosinopril, lisinopril, moexipril, perinodopril, quinapril, ramipril and trandolapril; inhibitors of the Na-K-ATPase membrane pump such as digoxin; neutralendopeptidase (NEP) inhibitors; ACE/NEP inhibitors such as omapatrilat, sampatrilat and fasidotril; angiotensin II antagonists such as candesartan, eprosartan, irbesartan, losartan, telmisartan and valsartan, in particular valsartan; renin inhibitors such as ditekiren, zankiren, terlakiren, aliskiren, RO 66-1132 and RO-66-1168; β-adrenergic receptor blockers such as acebutolol, atenolol, betaxolol, bisoprolol, metoprolol, nadolol, propranolol, sotalol and timolol; inotropic agents such as digoxin, dobutamine and milrinone; calcium channel blockers such as amlodipine, bepridil, diltiazem, felodipine, nicardipine, nimodipine, nifedipine, nisoldipine and verapamil; aldosterone receptor antagonists; and aldosterone synthase inhibitors;

agonists of peroxisome proliferator-activator receptors, such as fenofibrate, pioglitazone, rosiglitazone, tesaglitazar, BMS-298585, L-796449, the compounds specifically described in the patent application WO 2004/103995 i.e. compounds of examples 1 to or compounds specifically listed in claim 21, or the compounds specifically described in the patent application WO 03/043985 i.e. compounds of examples 1 to 7 or compounds specifically listed in claim 19 and especially (R)-1-{4-[5-methyl-2-(4-trifluoromethyl-phenyl)-oxazol-4-yl-methoxy]-benzenesulfonyl}-2,3-dihydro-1H-indole-2-carboxylic or a salt thereof; and the specific anti-diabetic compounds described in *Expert Opin Investig Drugs* 2003, 12(4): 623-633, FIGS. 1 to 7.

General Methods of Preparation

Specific methods for the preparation of the compounds of the invention are disclosed in detail below in the Examples.

In general, compounds of formula (I) may be prepared by the reaction schemes described below.

Compound of the invention in which ring A is a oxadiazole can be prepared by reacting the aniline (1) with 1,1'-thiocarbonyldipyridin-2(1H)-one (2). The isothiocyanate (3) is then reacted with carbohydrazides (4) to form the hydrazinecarbothioamide (5). Cyclization with 3-(ethyliminomethyleneamino)-N,N-dimethyl-propan-1-amine (EDC) to form a compound of the invention represented by formula I. Compounds represented by formula IA in which ring A is a oxadiazole and ring B is a phenyl can be prepared using the reactions of Scheme I but also in the alternative method shown in Scheme II and III.

Compounds represented by formula IA in which ring A is oxadiazole and B is phenyl can be prepared from the Suzuki coupling of the pinacol boronate ester (6) and the corresponding biphenyl bromide (7), as indicated in Scheme II. Alternatively, compounds represented by formula IA in which ring A is oxadizole and B is pyridine can be prepared by reacting the oxadiazole (8) with the corresponding pinacol boronate ester (9), as indicated in Scheme III.

Compounds represented by formula IIA in which ring A is a thiadiazoles can be prepared using the reactions in scheme 1. Cyclization of the hydrazinecarbothioamide with sulphuric acid in the presence of ethanol afford the compound of the invention represented by formula IIA.

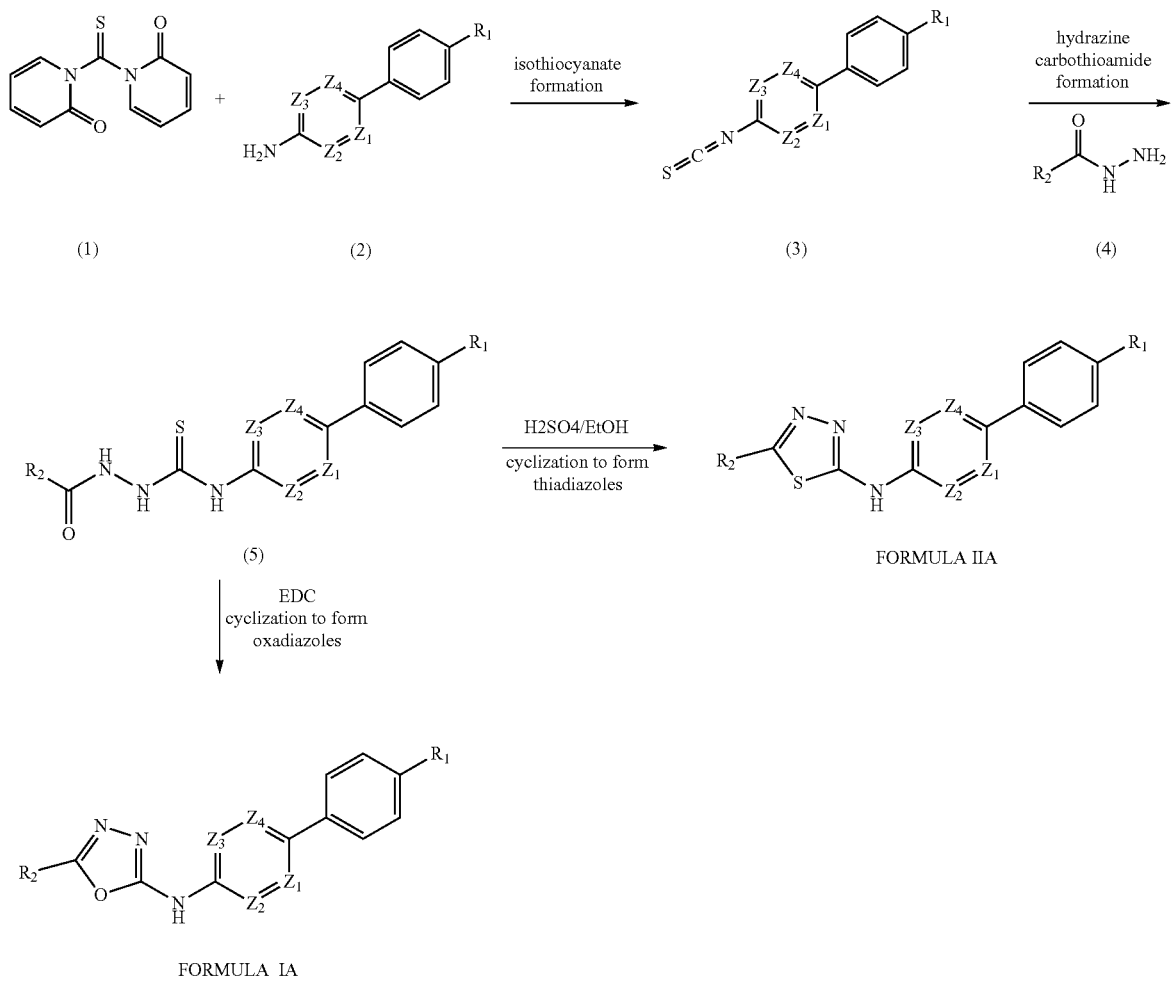

Scheme I: Method of preparing compounds of the invention wherein Ring A is a oxadiazoles or thiadiazoles

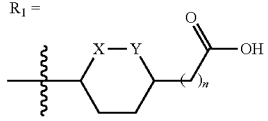

$R_2$ = alkyl or cycloalkyl

Scheme II: Alternate method of preparing compounds of the invention wherein Ring A is oxadiazole

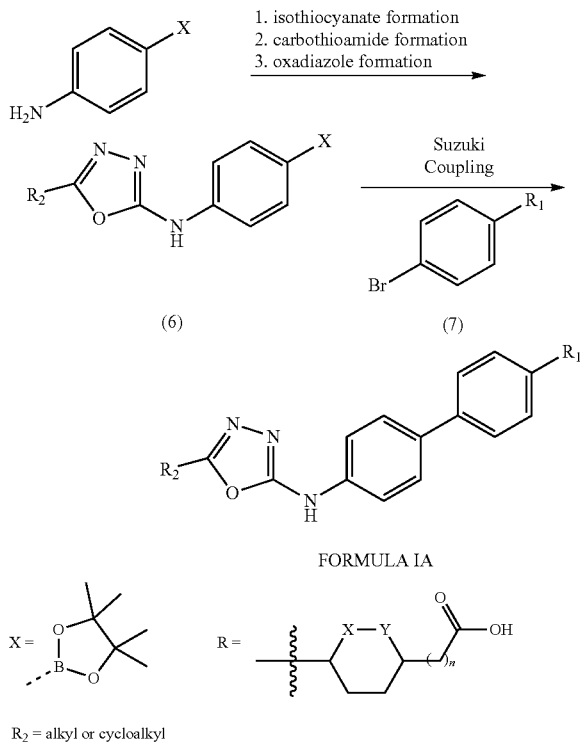

Scheme III: Alternate method of preparing compounds of the invention wherein Ring A is oxadiazole

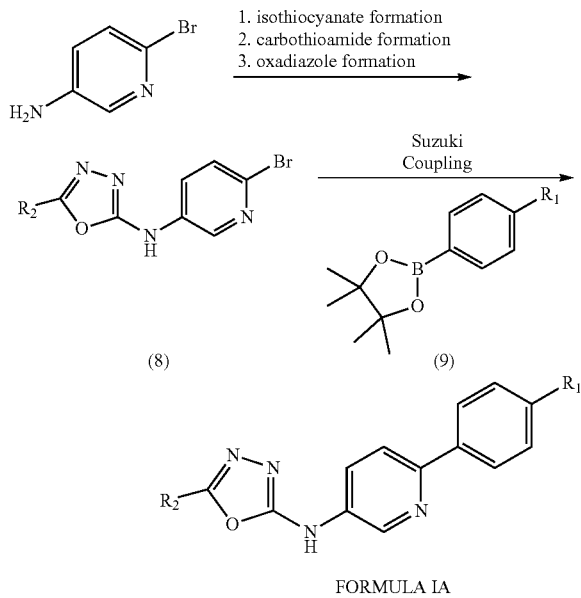

In general, compounds of formula (IV) and (V) may be prepared by the reaction schemes below.

Tetrahydro-2H-pyran-2-yl compounds can be prepared by alklyating the ester (38), followed by reduction to afford the alcohol (39). Metathesis with acrylate (40) generated the ester (41), which can be cyclised to form a compound of the invention represented by formula IXA.

Scheme IX: Method of preparing tetrahydro-2H-pyran-2-yl compounds

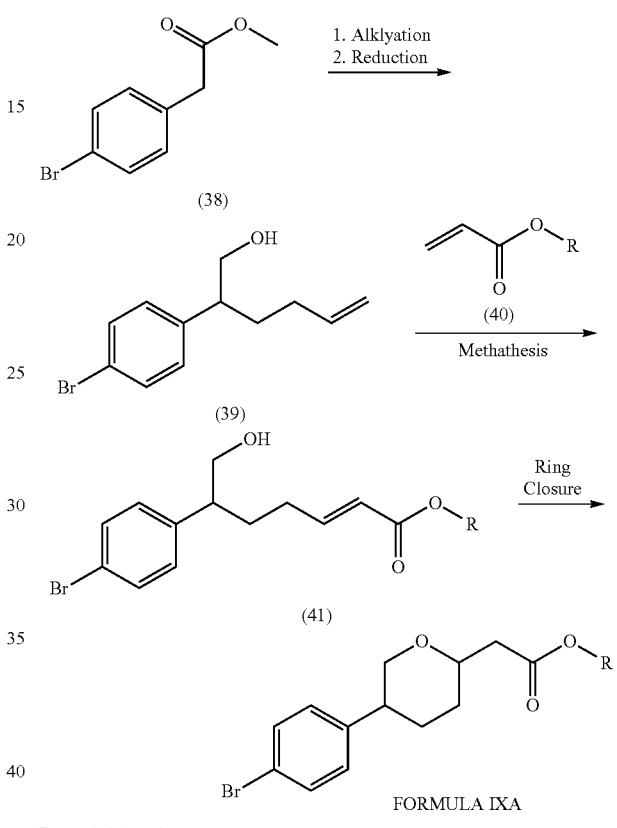

R = methyl, benzyl

In general, compounds of formula (XA) may be prepared by the reaction scheme below.

Tetrahydro-2H-pyran-3-yl compounds can be prepared by reacting the aldehyde (42) with the acetate reagent (43) via Stetter's condition, affording the dioxopentyl acetate (44). Deprotection afforded the intermediate (45), which can be cyclised and subsequently reduced to the tetrahydro-2H-pyrane (46). Oxidization, followed by Wittig reaction allowed a compound of the invention represented by XA.

Scheme X: Method of preparing tetrahydro-2H-pyran-3-yl compounds

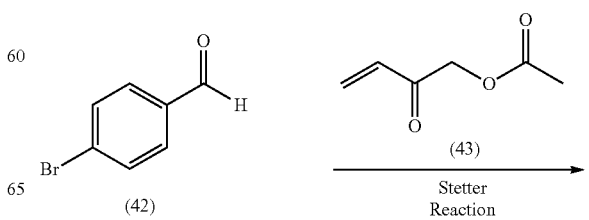

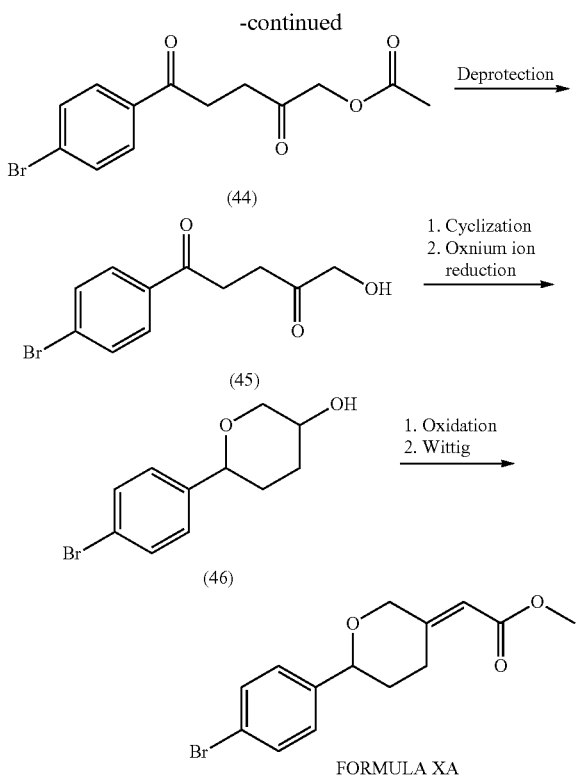

FORMULA XA

Chemical Groups

As used herein, the term "halogen" (or halo) refers to fluorine, bromine, chlorine or iodine, in particular fluorine, chlorine. Halogen-substituted groups and moieties, such as alkyl substituted by halogen (haloalkyl) can be mono-, poly- or per-halogenated.

As used herein, the term "hetero atoms" refers to nitrogen (N), oxygen (O) or sulfur (S) atoms, in particular nitrogen or oxygen.

As used herein, the term "alkyl" refers to a fully saturated branched or unbranched hydrocarbon moiety having up to 20 carbon atoms. Unless otherwise provided, alkyl refers to hydrocarbon moieties having 1 to 16 carbon atoms, 1 to 10 carbon atoms, 1 to 7 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like. A substituted alkyl is an alkyl group containing one or more, such as one, two or three substituents selected from halogen, hydroxy or alkoxy groups.

As used herein, the term "alkylene" refers to divalent alkyl group as defined herein above having 1 to 20 carbon atoms. It comprises 1 to 20 carbon atoms, Unless otherwise provided, alkylene refers to moieties having 1 to 16 carbon atoms, 1 to 10 carbon atoms, 1 to 7 carbon atoms, or 1 to 4 carbon atoms. Representative examples of alkylene include, but are not limited to, methylene, ethylene, n-propylene, iso-propylene, n-butylene, sec-butylene, iso-butylene, tert-butylene, n-pentylene, isopentylene, neopentylene, n-hexylene, 3-methylhexylene, 2,2-dimethylpentylene, 2,3-dimethylpentylene, n-heptylene, n-octylene, n-nonylene, n-decylene and the like.

A substituted alkylene is an alkylene group containing one or more, such as one, two or three substituents selected from halogen, hydroxy or alkoxy groups.

As used herein, the term "haloalkyl" refers to an alkyl as defined herein, which is substituted by one or more halo groups as defined herein. The haloalkyl can be monohaloalkyl, dihaloalkyl or polyhaloalkyl including perhaloalkyl. A monohaloalkyl can have one iodo, bromo, chloro or fluoro within the alkyl group. Dihaloalky and polyhaloalkyl groups can have two or more of the same halo atoms or a combination of different halo groups within the alkyl. Typically the polyhaloalkyl contains up to 12, or 10, or 8, or 6, or 4, or 3, or 2 halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Typically, alkoxy groups have 1-16, 1-10, 1-7, more preferably 1-4 carbon atoms.

A substituted alkoxy is an alkoxy group containing one or more, such as one, two or three substituents selected from halogen, hydroxy or alkoxy groups.

Similarly, each alkyl part of other groups like "alkylaminocrabonyl", "alkoxyalkyl", "alkoxycarbonyl", "alkoxy-carbonylalkyl", "alkylsulfonyl", "alkylsulfoxyl", "alkylamino", "haloalkyl" shall have the same meaning as described in the above-mentioned definition of "alkyl".

As used herein, the term "cycloalkyl" refers to saturated or unsaturated monocyclic, bicyclic, tricyclic or spirocyclic hydrocarbon groups of 3-12 carbon atoms. Unless otherwise provided, cycloalkyl refers to cyclic hydrocarbon groups having between 3 and 9 ring carbon atoms or between 3 and 7 ring carbon atoms.

A substituted cycloalkyl is a cycloylkyl group substituted by one, or two, or three, or more substituents independently selected from the group consisting of hydroxyl, thiol, cyano, nitro, oxo, alkylimino, $C_1$-$C_4$-alkyl, $C_1$-$C_4$-alkenyl, $C_1$-$C_4$-alkynyl, $C_1$-$C_4$-alkoxy, $C_1$-$C_4$-thioalkyl, $C_1$-$C_4$-alkenyloxy, $C_1$-$C_4$-alkynyloxy, halogen, $C_1$-$C_4$-alkylcarbonyl, carboxy, $C_1$-$C_4$-alkoxycarbonyl, amino, $C_1$-$C_4$-alkylamino, di-$C_1$-$C_4$-alkylamino, $C_1$-$C_4$-alkylaminocarbonyl, di-$C_1$-$C_4$-alkylaminocarbonyl, $C_1$-$C_4$-alkylcarbonylamino, $C_1$-$C_4$-alkylcarbonyl($C_1$-$C_4$-alkyl)amino, sulfonyl, sulfamoyl, alkylsulfamoyl, $C_1$-$C_4$-alkylaminosulfonyl where each of the afore-mentioned hydrocarbon groups (e.g., alkyl, alkenyl, alkynyl, alkoxy residues) may be further substituted by one or more residues independently selected at each occurrence from halogen, hydroxyl or $C_1$-$C_4$-alkoxy groups. Exemplary monocyclic hydrocarbon groups include, but are not limited to, cyclopropyl, cyclobutyl, cyclopentyl, cyclopentenyl, cyclohexyl and cyclohexenyl and the like. Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like. Exemplary tricyclic hydrocarbon groups include adamantyl and the like.

Similarly, each cycloalkyl part of other groups like "cycloalkyloxy", "cycloalkoxyalkyl", "cydoalkoxycarbonyl", "cycloalkoxy-carbonylalkyl", "cycloalkylsulfonyl", "halocycloalkyl" shall have the same meaning as described in the above-mentioned definition of "alkyl".

As used herein, the term "aryl" refers to an aromatic hydrocarbon group having 6-20 carbon atoms in the ring portion. Typically, aryl is monocyclic, bicyclic or tricyclic aryl having 6-20 carbon atoms. Furthermore, the term "aryl" as used herein, refers to an aromatic substituent which can be a single aromatic ring, or multiple aromatic rings that are fused together. Non-limiting examples include phenyl, naphthyl or tetrahydronaphthyl.

A substituted aryl is an aryl group substituted by 1-5 (such as one, or two, or three) substituents independently selected from the group consisting of hydroxyl, thiol, cyano, nitro, $C_1$-$C_4$-alkyl, $C_1$-$C_4$-alkenyl, $C_1$-$C_4$-alkynyl, $C_1$-$C_4$-alkoxy, $C_1$-$C_4$-thioalkyl, $C_1$-$C_4$-alkenyloxy, $C_1$-$C_4$-alkynyloxy, halogen, $C_1$-$C_4$-alkylcarbonyl, carboxy, $C_1$-$C_4$-alkoxycarbonyl, amino, $C_1$-$C_4$-alkylamino, di-$C_1$-$C_4$-alkylamino, $C_1$-$C_4$-alkylaminocarbonyl, di-$C_1$-$C_4$-alkylaminocarbonyl, $C_1$-$C_4$-alkylcarbonylamino, $C_1$-$C_4$-alkylcarbonyl($C_1$-$C_4$-alkyl)amino, sulfonyl, sulfamoyl, alkylsulfamoyl, $C_1$-$C_4$-alkylaminosulfonyl where each of the afore-mentioned hydrocarbon groups (e.g., alkyl, alkenyl, alkynyl, alkoxy residues) may be further substituted by one or more residues independently selected at each occurrence from halogen, hydroxyl or $C_1$-$C_4$-alkoxy groups.

Similarly, each aryl part of other groups like "aryloxy", "aryloxyalkyl", "aryloxycarbonyl", "aryloxy-carbonylalkyl" shall have the same meaning as described in the above-mentioned definition of "aryl".

As used herein, the term "heterocyclyl" refers to a heterocyclic radical that saturated or partially saturated and is preferably a monocyclic or a polycyclic ring (in case of a polycyclic ring particularly a bicyclic, tricyclic or spirocyclic ring); and has 3 to 24, more preferably 4 to 16, most preferably 5 to 10 and most preferably 5 or 6 ring atoms; wherein one or more, preferably one to four, especially one or two ring atoms are a heteroatom (the remaining ring atoms therefore being carbon). The bonding ring (i.e. the ring connecting to the molecule) preferably has 4 to 12, especially 5 to 7 ring atoms. The term heterocyclyl excludes heteroaryl. The heterocyclic group can be attached at a heteroatom or a carbon atom. The heterocyclyl can include fused or bridged rings as well as spirocyclic rings. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, and the like A substituted heterocyclyl is a heterocyclyl group independently substituted by 1-5 (such as one, or two, or three) substituents selected from hydroxyl, thiol, cyano, nitro, oxo, alkylimino, $C_1$-$C_4$-alkyl, $C_1$-$C_4$-alkenyl, $C_1$-$C_4$-alkynyl, $C_1$-$C_4$-alkoxy, $C_1$-$C_4$-thioalkyl, $C_1$-$C_4$-alkenyloxy, $C_1$-$C_4$-alkynyloxy, halogen, $C_1$-$C_4$-alkylcarbonyl, carboxy, $C_1$-$C_4$-alkoxycarbonyl, amino, $C_1$-$C_4$-alkylamino, di-$C_1$-$C_4$-alkylamino, $C_1$-$C_4$-alkylaminocarbonyl, di-$C_1$-$C_4$-alkylaminocarbonyl, $C_1$-$C_4$-alkylcarbonylamino, $C_1$-$C_4$-alkylcarbonyl($C_1$-$C_4$-alkyl)amino, sulfonyl, sulfamoyl, alkylsulfamoyl, $C_1$-$C_4$-alkylaminosulfonyl where each of the afore-mentioned hydrocarbon groups (e.g., alkyl, alkenyl, alkynyl, alkoxy residues) may be further substituted by one or more residues independently selected at each occurrence from halogen, hydroxyl or $C_1$-$C_4$-alkoxy groups.

Similarly, each heterocyclyl part of other groups like "heterocyclyloxy", "heterocyclyloxyalkyl", "heterocyclyloxycarbonyl" shall have the same meaning as described in the above-mentioned definition of "heterocyclyl".

As used herein, the term "heteroaryl" refers to a 5-14 membered monocyclic- or bicyclic- or tricyclic-aromatic ring system, having 1 to 8 heteroatoms. Typically, the heteroaryl is a 5-10 membered ring system (e.g., 5-7 membered monocycle or an 8-10 membered bicycle) or a 5-7 membered ring system. Typical heteroaryl groups include 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridyl, 3- or 4-pyridazinyl, 3-, 4-, or 5-pyrazinyl, 2-pyrazinyl, and 2-, 4-, or 5-pyrimidinyl.

The term "heteroaryl" also refers to a group in which a heteroaromatic ring is fused to one or more aryl, cycloaliphatic, or heterocyclyl rings, where the radical or point of attachment is on the heteroaromatic ring. Nonlimiting examples include 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, 2-, 4-, 5-, 6-, 7-, or 8-purinyl, 1-, 2-, 3-, 4-, 6-, 7-, 8-, or 9-quinolizinyl, 2-, 3-, 4-, 5-, 6-, 7-, or 8-quinoliyl, 1-, 3-, 4-, 5-, 6-, 7-, or 8-isoquinoliyl, 1-, 4-, 5-, 6-, 7-, or 8-phthalazinyl, 2-, 3-, 4-, 5-, or 6-naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4aH carbazolyl, 1-, 2-, 3-, 4-, 5-, 6-, 7-, or 8-carbzaolyl, 1-, 3-, 4-, 5-, 6-, 7-, 8-, or 9-carbolinyl, 1-, 2-, 3-, 4-, 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-, 8-, or 9-perimidinyl, 2-, 3-, 4-, 5-, 6-, 8-, 9-, or 10-phenathrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or l-, 3-, 4-, 5-, 6-, 7-, 8-, 9-, or 10-benzisoqinolinyl, 2-, 3-, 4-, or thieno[2,3-b]furanyl, 2-, 3-, 5-, 6-, 7-, 8-, 9-, 10-, or 11-7H-pyrazino[2,3-c]carbazolyl, 2-, 3-, 5-, 6-, or 7-2H-furo[3,2-b]-pyranyl, 2-, 3-, 4-, 5-, 7-, or 8-5H-pyrido[2,3-d]-o-oxazinyl, 1-, 3-, or 5-1H-pyrazolo[4,3-d]-oxazolyl, 2-, 4-, or 54H-imidazo[4,5-d]thiazolyl, 3-, 5-, or 8-pyrazino[2,3-d]pyridazinyl, 2-, 3-, 5-, or 6-imidazo[2,1-b]thiazolyl, 1-, 3-, 6-, 7-, 8-, or 9-furo[3,4-c]cinnolinyl, 1-, 2-, 3-, 4-, 5-, 6-, 8-, 9-, 10, or 11-4H-pyrido[2,3-c]carbazolyl, 2-, 3-, 6-, or 7-imidazo[1,2-b][1,2,4]triazinyl, 7-benzo[b]thienyl, 2-, 4-, 5-, 6-, or 7-benzoxazolyl, 2-, 4-, 5-, 6-, or 7-benzimidazolyl, 2-, 4-, 4-, 5-, 6-, or 7-benzothiazolyl, 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, or 11-1H-pyrrolo[1,2-b][2]benzazapinyl. Typical fused heteroary groups include, but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, and 2-, 4-, 5-, 6-, or 7-benzothiazolyl.

A substituted heteroaryl is a heteroaryl group containing one or more substituents selected from hydroxyl, thiol, cyano, nitro, $C_1$-$C_4$-alkyl, $C_1$-$C_4$-alkenyl, $C_1$-$C_4$-alkynyl, $C_1$-$C_4$-alkoxy, $C_1$-$C_4$-thioalkyl, $C_1$-$C_4$-alkenyloxy, $C_1$-$C_4$-alkynyloxy, halogen, $C_1$-$C_4$-alkylcarbonyl, carboxy, $C_1$-$C_4$-alkoxycarbonyl, amino, $C_1$-$C_4$-alkylamino, di-$C_1$-$C_4$-alkylamino, $C_1$-$C_4$-alkylaminocarbonyl, di-$C_1$-$C_4$-alkylaminocarbonyl, $C_1$-$C_4$-alkylcarbonylamino, $C_1$-$C_4$-alkylcarbonyl($C_1$-$C_4$-alkyl)amino, sulfonyl, sulfamoyl, alkylsulfamoyl, $C_1$-$C_4$-alkylaminosulfonyl where each of the afore-mentioned hydrocarbon groups (e.g., alkyl, alkenyl, alkynyl, alkoxy residues) may be further substituted by one or more residues independently selected at each occurrence from halogen, hydroxyl or $C_1$-$C_4$-alkoxy groups.

Similarly, each heteroaryl part of other groups like "heteroaryloxy", "heteroaryloxyalkyl", "heteroaryloxycarbonyl" shall have the same meaning as described in the above-mentioned definition of "heteroaryl".

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x means, for example, x±10%.

MODES FOR CARRYING OUT THE INVENTION

The following Examples are intended to illustrate the invention and are not to be construed as being limitations thereon. If not mentioned otherwise, all evaporations are performed under reduced pressure, between about 50 mmHg and 100 mmHg. The structure of final products, intermediates and starting materials is confirmed by standard analytical methods, e.g., microanalysis, melting point (m.p.) and spectroscopic characteristics, e.g. MS, IR and NMR.

Abbreviations used are those conventional in the art.

The structural formulae of the examples are shown in Annexe B.

HPLC Conditions:

Condition E (LC/MS Neutral Method)

LC-MS method with Broad range (5-95%) gradient with neutral mobile phase (5 mM NH4+HCOO—). Electrospray mass spectra (+) and (−), DAD-UV chromatogram 210-400 nm, Gradient: 5-95% MeCN in 2 min (2 mL/min), 2 μL injection. Column: Inertsil C8-3, 3.0×433 mm×3.0 μm, 40 deg C.

Condition L (HR/MS with Purity Assessment)

1.0 mL/min flow rate with the gradient from 2% to 98% ACN in 4.40 min, 3.75 mM Ammonium Acetate and 0.0005% Formic Acid used as the modifier additive in the Aqueous Phase. 0.04% of Formic Acid used as the modifier in the Organic Phase. Acquity UPLC CSH C18 2.1×50 mm 1.7 um column at 50 deg C., LCUV/ESI-MS data was recorded on an Acquity G2 Xevo QT of with resolution of >20000 (FWHM).

Condition M (Purity Neutral Method)

1.0 mL/min flow rate with the gradient from 2% to 98% ACN in 4.40 min, 3.75 mM Ammonium Acetate and 2% acetonitrile used as the modifier additive in the Aqueous Phase. No additive was used as the modifier in the Organic Phase. Acquity UPLC CSH C18 2.1×50 mm 1.7 um column at 50 deg C.

Condition R (LC/MS Neutral Method)

LC-MS method with Broad range (5-95%) gradient with neutral mobile phase (5 mM NH4+HCOO—). Electrospray mass spectra (+) and (−), DAD-UV chromatogram 210-400 nm, Gradient: 5-95% MeCN in 2 min (2 mL/min), 2 μL injection. Column: X-bridge C18, 3.0 cm×30 mm×3.5 μm, 40° C.

Condition W (LC/MS Acidic Method)

1.0 mL/min flow rate with the gradient from 2% to 98% ACN in 1.70 min, 3.75 mM Ammonium Acetate and 0.05% Formic Acid used as the modifier additive in the Aqueous Phase. 0.04% of Formic Acid used as the modifier in the Organic Phase. Acquity UPLC BEH C18 2.1×50 mm 1.7 um column at 50 deg C.

Condition X (UPLC Neutral Method with MS)

1.0 mL/min flow rate with the gradient from 2% to 98% ACN in 1.70 min, 3.75 mM Ammonium Acetate and 2% acetonitrile used as the modifier additive in the aqueous phase. 0.04% ammonium acetate was used as the modifier in the Organic Phase. Acquity UPLC CSH C18 2.1×50 mm 1.7 um column at 50 deg C.

Condition Y (SFC, Chiral Method for e.e. Determination)

5.0 ml/min flow rate with gradient from 5% to 55% MeOH in $CO_2$. CelLUX2, 5 uM, 4.6×100 mm column at 40 deg C.

| | MW | Structure | | IUPAC Name |
|---|---|---|---|---|
| Ex 1 | 489.44 | 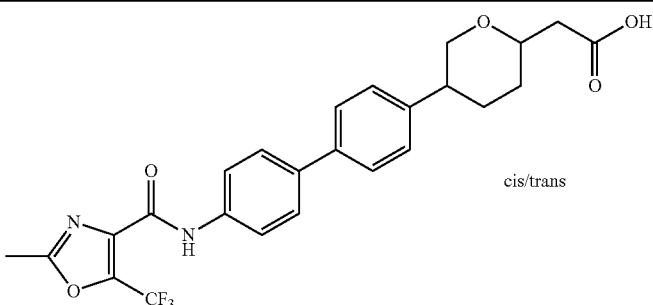 cis/trans | | 2-(5-(4'-(2-methyl-5-(trifluoromethyl)oxazole-4-carboxamido)-[1,1'-biphenyl]-4-yl)tetrahydro-2H-pyran-2-yl)acetic acid, racemate |
| Ex 2 | 489.44 | 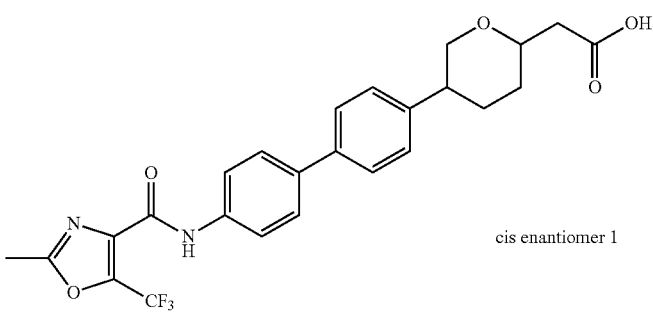 [SMILES: Cc1nc(C(=O)Nc2ccc(-c3ccc(C4CCC(CC(=O)O)OC4)cc3)cc2)c(C(F)(F)F)o1] cis enantiomer 1 | | 2-(5-(4'-(2-methyl-5-(trifluoromethyl)oxazole-4-carboxamido)-[1,1'-biphenyl]-4-yl)tetrahydro-2H-pyran-2-yl)acetic acid, cis enantiomer 1 |

-continued

| | MW | Structure | IUPAC Name |
|---|---|---|---|
| Ex 3 | 489.44 | trans enantiomer 1 | 2-(5-(4'-(2-methyl-5-(trifluoromethyl)oxazole-4-carboxamido)-[1,1'-biphenyl]-4-yl)tetrahydro-2H-pyran-2-yl)acetic acid, trans enantiomer 1 |
| Ex 4 | 489.44 | trans enantiomer 2 | 2-(5-(4'-(2-methyl-5-(trifluoromethyl)oxazole-4-carboxamido)-[1,1'-biphenyl]-4-yl)tetrahydro-2H-pyran-2-yl)acetic acid, trans enantiomer 2 |
| Ex 5 | 489.44 | cis enantiomer 2 | 2-(5-(4'-(2-methyl-5-(trifluoromethyl)oxazole-4-carboxamido)-[1,1'-biphenyl]-4-yl)tetrahydro-2H-pyran-2-yl)acetic acid, cis enantiomer 2 |
| Ex 6 | 433.50 | cis/trans | 2-(5-(4'-((5-cyclobutyl-1,3,4-oxadiazol-2-yl)amino)-[1,1'-biphenyl]-4-yl)tetrahydro-2H-pyran-2-yl)acetic acid, racemate |
| Ex 7 | 456.49 | cis/trans | 2-(6-(4'-((5-cyclobutyl-1,3,4-oxadiazol-2-yl)amino)-[1,1'-biphenyl]-4-yl)tetrahydro-2H-pyran-3-yl)acetic acid, sodium salt, racemate |

|     | MW | Structure | IUPAC Name |
| --- | --- | --- | --- |
| Ex 8 | 433.50 | 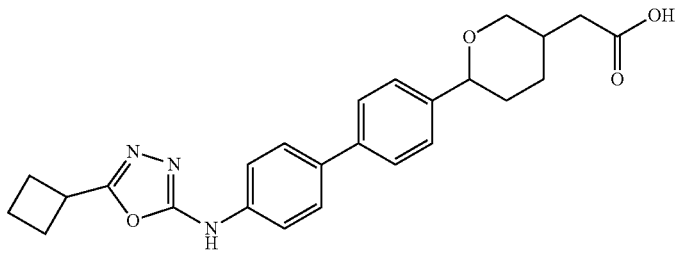<br>cis enantiomer 1 | 2-(6-(4'-((5-cyclobutyl-1,3,4-oxadiazol-2-yl)amino)-[1,1'-biphenyl]-4-yl)tetrahydro-2H-pyran-3-yl)acetic acid, cis enantiomer 1 |
| Ex 9 | 433.50 | 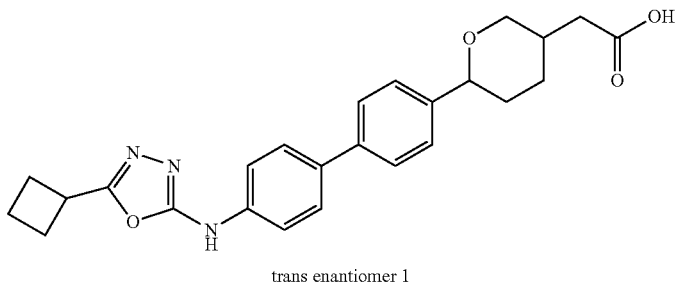 [SMILES: O=C(O)CC1CCC(c2ccc(-c3ccc(Nc4nnc(C5CCC5)o4)cc3)cc2)OC1]<br>trans enantiomer 1 | 2-(6-(4'-((5-cyclobutyl-1,3,4-oxadiazol-2-yl)amino)-[1,1'-biphenyl]-4-yl)tetrahydro-2H-pyran-3-yl)acetic acid, trans enantiomer 1 |
| Ex 10 | 433.50 | 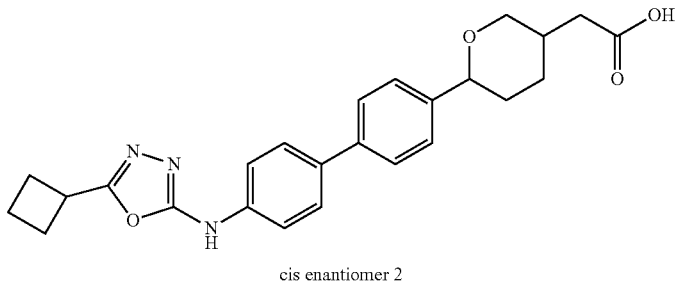 [SMILES: O=C(O)CC1CCC(c2ccc(-c3ccc(Nc4nnc(C5CCC5)o4)cc3)cc2)OC1]<br>cis enantiomer 2 | 2-(6-(4'-((5-cyclobutyl-1,3,4-oxadiazol-2-yl)amino)-[1,1'-biphenyl]-4-yl)tetrahydro-2H-pyran-3-yl)acetic acid, cis enantiomer 2 |
| Ex 11 | 433.50 | 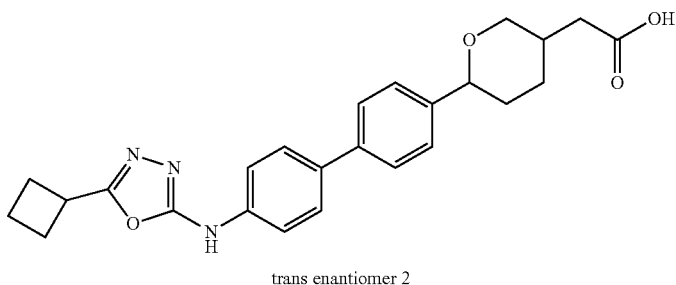 [SMILES: O=C(O)CC1CCC(c2ccc(-c3ccc(Nc4nnc(C5CCC5)o4)cc3)cc2)OC1]<br>trans enantiomer 2 | 2-(6-(4'-((5-cyclobutyl-1,3,4-oxadiazol-2-yl)amino)-[1,1'-biphenyl]-4-yl)tetrahydro-2H-pyran-3-yl)acetic acid, trans enantiomer 2 |

Example 1-5

2-(5-(4'-(2-methyl-5-(trifluoromethyl)oxazole-4-carboxamido)-[1,1'-biphenyl]-4-yl)tetrahydro-2H-pyran-2-yl)acetic acid

Step 1. Synthesis of Methyl 2-(4-bromophenyl)hex-5-enoate

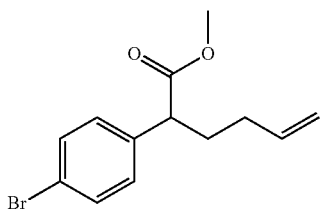 [SMILES: C=CCCC(C(=O)OC)c1ccc(Br)cc1]

To a solution of methyl 4-bromophenylacetate (1 g, 4.37 mmol) in DMF (12 ml) at room temperature was added 60% NaH (0.227 g, 5.68 mmol) and the mixture was stirred at room temperature for 1 hr then was added 4-bromo-1-butene (0.487 ml, 4.80 mmol). The reaction was stirred at room temperature overnight. The reaction was quenched by sat. aq. NH4Cl and was extracted with EtOAc. The combined organic layer was washed with brine and dried over anhydrous sodium sulfate, filtered and concentrated. The residue was purified by flash chromatography (0 to 30% DCM/Hep) to give the title compound 1.1 g (yield 89%). Retention time 1.54 min (condition A).

Step 2. Synthesis of 2-(4-Bromophenyl)hex-5-en-1-ol

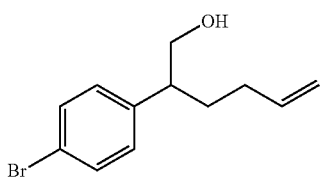

To a solution of methyl 2-(4-bromophenyl)hex-5-enoate (870 mg, 3.07 mmol) in DCM (15 ml) at −78° C. was added DIBAL-H/toluene (7.68 ml, 7.68 mmol) drop wise and the mixture was stirred at room temperature for 30 min. The reaction was quenched by the addition of 1.8 mL pH 8 buffered sat. NH4Cl solution (prepared by mixing 1.2 mL NH4OH and 20 mL sat. NH4Cl) at −78° C. and let stir and warm to room temperature for 45 min. To this mixture was added 1.6 g MgSO4 and the reaction was stirred at room temperature for another 30 min to afford a thick slurry, which was filtered to give a clear and colorless oil: half aldehyde and half alcohol.

To a solution of the above mixture in MeOH (10 ml) at 0° C. was added NaBH4 (137 mg, 3.62 mmol) and the mixture was stirred at room temperature for 30 min. The mixture was concentrated down and the residue was purified by flash chromatography (5 to 30% Acetone/Heptane) to give the title compound 530 mg (yield 68%). Retention time 1.37 min (condition A).

Step 3. Synthesis of benzyl 6-(4-bromophenyl)-7-hydroxyhept-2-enoate

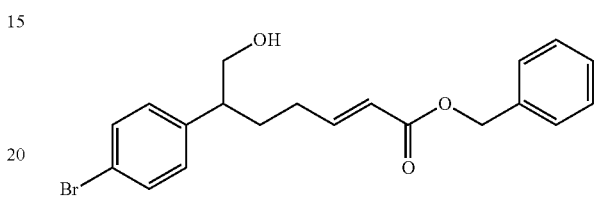

To a degassed solution of 2-(4-bromophenyl)hex-5-en-1-ol (108 mg, 0.423 mmol) in DCM (5 ml) at room temperature was added benzyl acrylate (0.191 ml, 1.270 mmol) and GrubbsII (35.9 mg, 0.042 mmol) and the mixture was stirred at 40° C. for 30 min. The mixture was concentrated and the residue was purified by flash chromatography (5 to 40% Acetone/Heptane) to give the title compound 130 mg (yield 79%). MS (ESI) m/z 490.4 (M+1). Retention time 1.49 min (condition A).

Step 4. Synthesis of benzyl 2-(5-(4-bromophenyl) tetrahydro-2H-pyran-2-yl)acetate

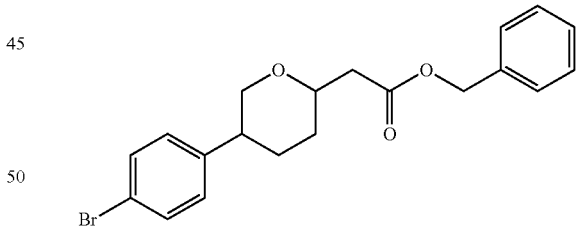

To a solution of benzyl 6-(4-bromophenyl)-7-hydroxyhept-2-enoate (516 mg, 1.326 mmol) in dioxane (20 ml) at room temperature was added 60% NaH (106 mg, 2.65 mmol) and the mixture was stirred at 60° C. for 3 hr. Small amount of title compound was formed with the major SM. So the reaction was added more NaH and heated at 60° C. overnight. The reaction was quenched by sat. aq. NH4Cl and was extracted with EtOAc. The combined organic layer was washed with brine and dried over anhydrous sodium sulfate, filtered and concentrated. The residue was purified by flash chromatography (5 to 100% Acetone/Heptane) to give the title compound 380 mg (yield 74%). MS (ESI) m/z 391.2 (M+2). Retention time 1.62 min (condition A).

Step 5. Synthesis of benzyl 2-(5-(4'-amino-[1,1'-biphenyl]-4-yl)tetrahydro-2H-pyran-2-yl)acetate

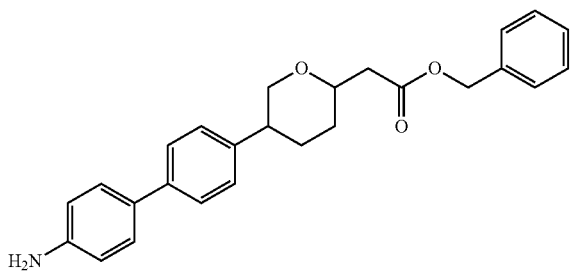 [SMILES: Nc1ccc(-c2ccc(C3CCC(CC(=O)OCc4ccccc4)OC3)cc2)cc1]

To a solution of benzyl 2-(5-(4-bromophenyl)tetrahydro-2H-pyran-2-yl)acetate (300 mg, 0.771 mmol) in dioxane (6 ml) at room temperature was added 4-aminophenylboronic acid (211 mg, 1.541 mmol), Pd(Ph3P)4 (178 mg, 0.154 mmol) and 2M Na2CO3 (1.541 ml, 3.08 mmol) and the mixture was degassed and heated at 120° C. in microwave for 30 min. The reaction was quenched by sat. aq. NH4Cl and was extracted with EtOAc. The combined organic layer was washed with brine and dried over anhydrous sodium sulfate, filtered and concentrated. The residue was purified by flash chromatography (10 to 50% EtOAc (2% TEA)/Heptane) to give the title compound 250 mg (yield 81%). MS (ESI) m/z 402.3 (M+1). Retention time 1.48 min (condition A).

Step 6. Synthesis of benzyl 2-(5-(4'-(2-methyl-5-(trifluoromethyl)oxazole-4-carboxamido)-[1,1'-biphenyl]-4-yl)tetrahydro-2H-pyran-2-yl)acetate

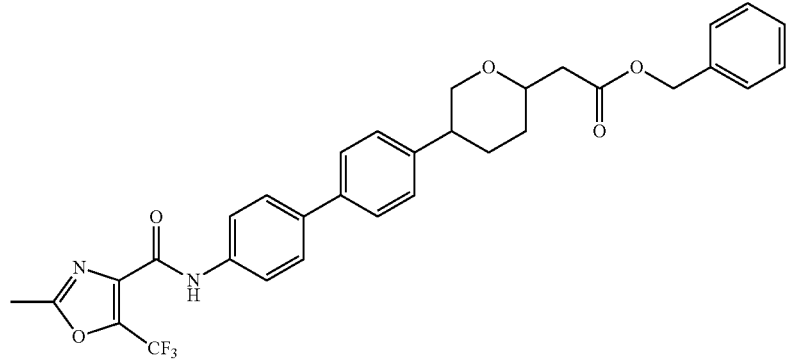 [SMILES: Cc1nc(C(=O)Nc2ccc(-c3ccc(C4CCC(CC(=O)OCc5ccccc5)OC4)cc3)cc2)c(C(F)(F)F)o1]

To a solution of benzyl 2-(5-(4'-amino-[1,1'-biphenyl]-4-yl)tetrahydro-2H-pyran-2-yl)acetate (118 mg, 0.294 mmol) in DMF (2 ml) at room temperature was added 2-methyl-5-(trifluoromethyl)oxazole-4-carboxylic acid (74.5 mg, 0.382 mmol) and DIPEA (0.103 ml, 0.588 mmol) and the reaction was stirred at room temperature for 10 min then was added HATU (145 mg, 0.382 mmol). The reaction was stirred at room temperature for 30 min. The reaction was quenched by brine and was extracted with EtOAc. The combined organic layer was washed with brine and dried over anhydrous sodium sulfate, filtered and concentrated. The residue was purified by flash chromatography (10 to 50% EtOAc/Heptane) to give the title compound 138 mg (yield 81%). MS (ESI) m/z 579.4 (M+1). Retention time 1.69 min (condition A).

Step 7. Synthesis of 2-(5-(4'-(2-Methyl-5-(trifluoromethyl)oxazole-4-carboxamido)-[1,1'-biphenyl]-4-yl)tetrahydro-2H-pyran-2-yl)acetic acid

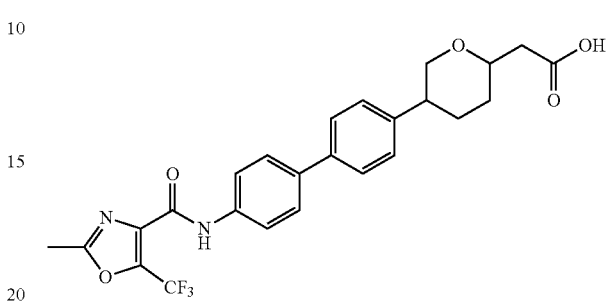

Benzyl 2-(5-(4'-(2-methyl-5-(trifluoromethyl)oxazole-4-carboxamido)-[1,1'-biphenyl]-4-yl)tetrahydro-2H-pyran-2-yl)acetate was dissolved in EtOAc and hydrogenated with 10% Pd(OH)2/C under H2 balloon for 30 min. The reaction mixture was filtered off to remove the catalyst and the filtrate was concentrated. The residue was purified by reverse HPLC (8 to 50% ACN-water (0.1% NH40H) with X-bridge C8 column) to give the title compound 93 mg (yield 80%) as a mixture of cis/trans isomer (ratio of 1:3). After chiral SFC separation (CL2-20×250 mm, isocratic 45% MeOH in CO2, 75% g/min flow, 220 nM UV) afforded the cis and trans enantiomes:

trans enantiomer 1: HR/MS [M+H]$^+$: found 489.1655, calc. 489.1637. RT: 2.48 (Condition L). 99.4% e.e. (Condition Y). $^1$H NMR (400 MHz, DMSO-d$_6$) δ ppm 1.33-1.48 (m, 1H), 1.74-1.99 (m, 3H), 2.30-2.44 (m, 2H), 2.62 (s, 3H), 2.71-2.83 (m, 1H), 3.35-3.44 (m, 1H), 3.75 (dt, J=11.12, 5.81 Hz, 1H), 3.86 (dt, J=13.14, 1.89 Hz, 1H), 7.34 (d, J=8.34 Hz, 2H), 7.55-7.70 (m, 4H), 7.84-7.93 (m, 2H), 10.66 (s, 1H), 12.16 (br. s., 1H).

cis enantiomer 1: HR/MS [M+H]$^+$: found 489.1559, calc. 489.1637. RT: 2.51 (Condition L). 100% e.e. (Condition Y). $^1$H NMR (400 MHz, DMSO-d$_6$) δ ppm 1.33-1.46 (m, 1H), 1.52-1.62 (m, 1H), 1.86-2.05 (m, 2H), 2.43-2.48 (m, 2H), 2.63 (s, 3H), 2.84 (t, J=3.79 Hz, 1H), 3.75 (dd, J=11.75, 3.41 Hz, 1H), 3.84-3.94 (m, 1H), 4.04 (dd, J=11.75, 2.91 Hz, 1H), 7.50 (d, J=8.34 Hz, 2H), 7.56-7.63 (m, 2H), 7.63-7.70 (m, 2H), 7.86-7.94 (m, 2H), 10.66 (s, 1H).

After another chiral SFC separation (AD-H 20×25 mm, isocratic 40% IPA+5 mM NH4OH in CO2, 75 g/min flow, 220 nM UV) afforded the other cis and trans enantiomers:

trans enantiomer 2: HR/MS [M+H]⁺: found 489.1623, calc. 489.1637. RT: 2.05 (Condition L). 98.39% e.e. (Condition Y). $^1$H NMR (400 MHz, DMSO-$d_6$) δ ppm 1.33-1.46 (m, 1H), 1.75-1.99 (m, 3H), 2.31-2.46 (m, 2H), 2.62 (s, 3H), 2.77 (ddt, J=15.38, 7.61, 3.79, 3.79 Hz, 1H), 3.38-3.43 (m, 1H), 3.75 (dt, J=11.05, 5.72 Hz, 1H), 3.82-3.90 (m, 1H), 7.34 (d, J=8.34 Hz, 2H), 7.55-7.67 (m, 4H), 7.89 (d, J=8.84 Hz, 2H), 10.65 (s, 1H).

cis enatiomer 2: HR/MS [M+H]⁺: found 489.1618, calc. 489.1637. RT: 2.02 (Condition L). 97.3% e.e. (Condition Y). $^1$H NMR (400 MHz, DMSO-$d_6$) δ ppm 1.34-1.45 (m, 1H), 1.52-1.62 (m, 1H), 1.87-2.05 (m, 2H), 2.42-2.47 (m, 2H), 2.63 (s, 3H), 2.84 (t, J=3.92 Hz, 1H), 3.75 (dd, J=11.62, 3.28 Hz, 1H), 3.83-3.94 (m, 1H), 4.03 (dd, J=11.62, 3.03 Hz, 1H), 7.50 (d, J=8.34 Hz, 2H), 7.57-7.69 (m, 4H), 7.85-7.94 (m, 2H), 10.66 (s, 1H).

Example 6

2-(5-(4'-((5-cyclobutyl-1,3,4-oxadiazol-2-yl)amino)-[1,1'-biphenyl]-4-yl)tetrahydro-2H-pyran-2-yl)acetic acid Step 1. Synthesis of benzyl 2-(5-(4'-((5-cyclobutyl-1,3,4-oxadiazol-2-yl)amino)-[1,1'-biphenyl]-4-yl)tetrahydro-2H-pyran-2-yl)acetate

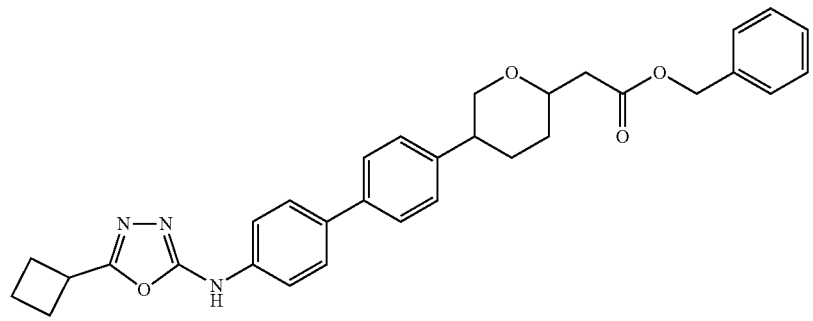 [SMILES: O=C(CC1CCC(c2ccc(-c3ccc(Nc4nnc(C5CCC5)o4)cc3)cc2)CO1)OCc1ccccc1]

To a solution of benzyl 2-(5-(4'-amino-[1,1'-biphenyl]-4-yl)tetrahydro-2H-pyran-2-yl)acetate (132 mg, 0.329 mmol) in DCM (5 ml) at room temperature was added 1,1'-thiocarbonyldipyridin-2(1H)-one (84 mg, 0.362 mmol) and the reaction was stirred at room temperature. 10 min the 1st step was done. To the mixture was added cyclobutanecarbohydrazide (75 mg, 0.658 mmol) and the mixture was stirred at room temperature until the 2nd step was done. To the mixture was added EDC.HCl (189 mg, 0.986 mmol) and the reaction was stirred at room temperature until done. The residue was purified by flash chromatography (10 to 60% EtOAc/Heptane) to give the title compound. MS (ESI) m/z 524.4 (M+1). Retention time 1.56 min (condition A).

Step 2. Synthesis of 2-(5-(4'-((5-cyclobutyl-1,3,4-oxadiazol-2-yl)amino)-[1,1'-biphenyl]-4-yl)tetrahydro-2H-pyran-2-yl)acetic acid

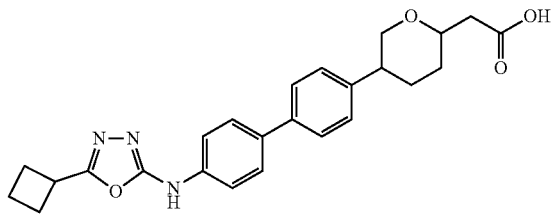 [SMILES: O=C(O)CC1CCC(c2ccc(-c3ccc(Nc4nnc(C5CCC5)o4)cc3)cc2)CO1]

Benzyl 2-(5-(4'-((5-cyclobutyl-1,3,4-oxadiazol-2-yl)amino)-[1,1'-biphenyl]-4-yl)tetrahydro-2H-pyran-2-yl)acetate was dissolved in EtOAc and hydrogenated with 10% Pd(OH)2/C under H2 balloon for 1 hr. The reaction mixture was filtered off to remove the catalyst and the filtrate was concentrated. The residue was purified by reverse HPLC (10 to 50% ACN-water (0.1% NH4OH) with X-bridge C8 column) to give the title compound 19.8 mg. HR/MS [M+H]⁺: found 434.2060, calc. 434.2080. RT: 2.61 (Condition L). The ratio of cis to trans was determined to be ~1.1:1 by NMR studies. cis-isomer: $^1$H NMR (400 MHz, DMSO-$d_6$) δ ppm 1.33-1.47 (m, 1H), 1.51-1.62 (m, 1H), 1.86-2.13 (m, 4H), 2.27-2.46 (m, 6H), 2.83 (t, J=3.79 Hz, 1H), 3.62-3.79 (m, 2H), 3.81-3.94 (m, 1H), 4.02 (dd, J=11.62, 3.28 Hz, 1H), 7.48 (d, J=8.34 Hz, 2H), 7.53-7.68 (m, 6H), 10.50 (br. s., 1H). trans-isomer $^1$H NMR (400 MHz, DMSO-$d_6$) δ ppm 1.31-1.47 (m, 1H), 1.73-2.13 (m, 5H), 2.24-2.46 (m, 6H), 2.75 (ddd, J=11.37, 7.45, 4.17 Hz, 1H), 3.35-3.44 (m, 1H), 3.62-3.79 (m, 2H), 3.81-3.94 (m, 1H), 7.32 (d, J=8.34 Hz, 2H), 7.53-7.68 (m, 6H), 10.50 (br. s., 1H).

Example 7-11

2-(6-(4'-((5-cyclobutyl-1,3,4-oxadiazol-2-yl)amino)-[1,1'-biphenyl]-4-yl)tetrahydro-2H-pyran-3-yl)acetic acid sodium salt Step 1. Synthesis of 5-(4-bromophenyl)-2,5-dioxopentyl acetate

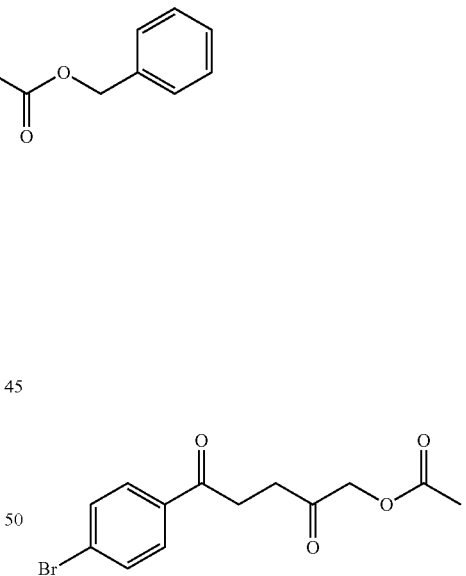

To a round bottom flask containing 4-bromobenzaldehyde (1.4 g, 7.80 mmol), 2-oxobut-3-enyl acetate (1 g, 7.80 mmol) and 3-benzyl-5-(2-hydroxyethyl)-4-methyl-thiazolium chloride (0.21 g, 0.78 mmol) was added dioxane (20 ml). The mixture was stirred at room temperature and triethylamine (0.65 ml, 0.60 mmol) was added. The reaction mixture was heated to 80 C for overnight. Afterward, the reaction was cooled down to room temperature, quenched with a solution of saturated ammonium chloride and concentrated. The residue was taken up in MTBE and washed with saturated ammonium chloride solution twice, then once with brine. The organic portion was dried over sodium sulfate, filtered and concentrated. The resulting crude material was purified by column chromatography to afford the title compound as a light orange solid after drying (1.63 g, 67% yield). MS (ESI) m/z 315.0 (M+1). Retention time 1.14 min. (Condition X).

Step 2. Synthesis of
1-(4-bromophenyl)-5-hydroxypentane-1,4-dione

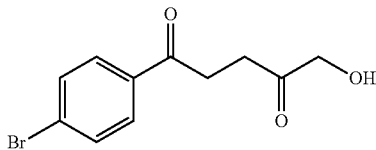 [SMILES: O=C(CO)CCC(=O)c1ccc(Br)cc1]

To a round bottom flask containing 5-(4-bromophenyl)-2, 5-dioxopentyl acetate (1.3 g, 4.15 mmol) and sodium bicarbonate (0.42 g, 4.98 mmol) was added MeOH (26 ml). The mixture was stir at room temperature for 19 hours. Afterward, the reaction mixture was concentrated and the resulting residue was taken up in water to form a slurry. The slurry was filtered, washed with water to afford the title compound as off-white solid after drying (985 mg, 88% yield). MS (ESI) m/z 273.0 (M+1). Retention time 1.10 min. (Condition R).

Step 3. Synthesis of
6-(4-bromophenyl)tetrahydro-2H-pyran-3-ol

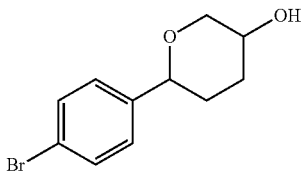 [SMILES: OC1CCC(c2ccc(Br)cc2)OC1]

To a round bottom flask containing 1-(4-bromophenyl)-5-hydroxypentane-1,4-dione (800 mg, 2.95 mmol) was added DCM (40 ml). The solution was cooled under an ice-bath and a solution of Boron trifluoride (diethyl ether complex, 0.89 ml, 7.00 mmol) was added dropwise. After the addition, triethylsilane (1.11 ml, 6.96 mmol) was also added and the reaction was stirred in an ice-bath for 85 minutes. The mixture was quenched with a saturated of NaHCO$_3$ and was extracted twice with DCM. The combined organic portions was dried over sodium sulfate, filtered and concentrated to afford a crude residue. Column purification afforded the title compound as thick oil (638 mg, 84% conversion). MS (ESI) m/z, non-ionizable. Retention time 1.17 min. (Condition X).

Step 4. Synthesis of
6-(4-bromophenyl)dihydro-2H-pyran-3(4H)-one

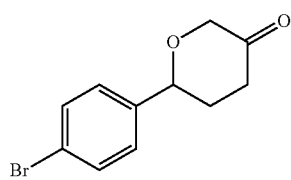 [SMILES: O=C1CCC(c2ccc(Br)cc2)OC1]

To a round bottom flask containing 6-(4-bromophenyl) tetrahydro-2H-pyran-3-ol (638 mg, 2.48 mmol) was added DCM (16 ml). The mixture was stirred at room temperature before Dess-Martin Periodonane (1.3 g, 2.98 mmol) was added in several portions. After the addition, the reaction mixture was stirred for 2 hours before being quenched by a solution of saturated NaHCO$_3$. The organic layer was washed with saturated NaHCO$_3$ twice, then brine. The organic portion was dried over sodium sulfate, filtered and concentrated to afford a crude oil. Column purification afforded the title compound as a thick oil after drying (126 mg, 20% yield). $^1$H NMR (400 MHz, CHLOROFORM-d) δ ppm 7.50-7.55 (m, 2H) 7.26-7.32 (m, 2H) 4.75 (dd, J=10.61, 2.78 Hz, 1H) 4.27-4.36 (m, 1H) 4.14-4.22 (m, 1H) 2.59-2.77 (m, 2H) 2.35 (ddt, J=13.74, 6.60, 3.35, 3.35 Hz, 1H) 2.11-2.24 (m, 1H).

Step 5. Synthesis of (E/Z)-methyl 2-(6-(4-bromophenyl)-2H-pyran-3(4H,5H,6H)-ylidene)acetate

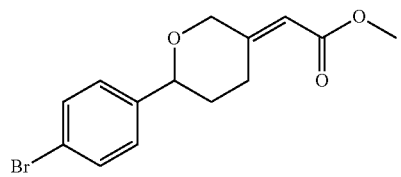 [SMILES: COC(=O)/C=C1\CCC(c2ccc(Br)cc2)OC1]

To a solution of NaH (60% in mineral oil, 23.4 mg, 0.59 mmol) in methanol (1.5 mL) was added trimethylphosphonoacetate (99 mg, 0.54 mmol) and the reaction was stirred at room temperature for 30 minutes. To the reaction was added a solution of 6-(4-bromophenyl)dihydro-2H-pyran-3(4H)-one (115 mg, 0.45 mol in 1.5 ml MeOH) and the reaction was stirred room temperature for 2 hours. The resulting reaction mixture was quenched with a solution of saturated ammonium chloride and extracted with DCM. The organic phase was dried over sodium sulfate, filtered and concentrated to afford a crude oil. After column purification afforded the title compound as a low melting solid after drying (83 mg, 59% yield). MS (ESI) m/z 313.0 (M+1). Retention time 1.55 min. (Condition R).

Step 6. Synthesis of (E/Z)-methyl 2-(6-(4'-nitrobiphenyl-4-yl)-2H-pyran-3(4H,5H,6H)-ylidene)acetate

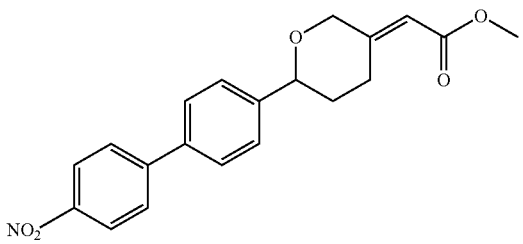 [SMILES: COC(=O)/C=C1\CCC(c2ccc(-c3ccc([N+](=O)[O-])cc3)cc2)OC1]

To a mixture of (E/Z)-methyl 2-(6-(4-bromophenyl)-2H-pyran-3(4H,5H,6H)-ylidene)acetate (83 mg, 0.27 mmol), 4-nitrophenylboronic acid (53.4 mg, 0.32 mmol) and Pd$_3$(PPh$_3$)$_4$ (12.3 mg, 4 mol %) was added dimethoxyethane (2.5 ml) at room temperature. With stirring, a solution of Na$_2$CO$_3$ (2N, 1.07 ml, 1.07 mmol) was added and the mixture was radiated in a microwave to 120° C. for 20 minutes. After cooling to room temperature, the reaction mixture was concentrated to dryness. The residue was taken up in DCM and dried over sodium sulfate. The content was filtered through a pad of celite and the filtrate concentrated to afford a crude material, which was purified by column chromatography to afford the title compound as a yellow solid after drying (81 mg, 86% yield). MS (ESI) m/z 354.1 (M+1). Retention time 1.60 min. (Condition R).

Step 7. Synthesis of methyl 2-(6-(4'-aminobiphenyl-4-yl)tetrahydro-2H-pyran-3-yl)acetate

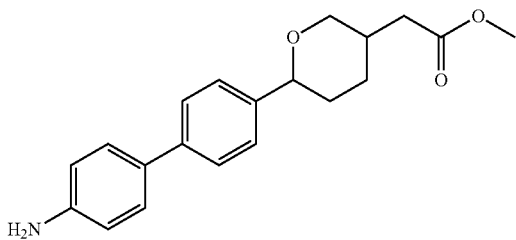 [SMILES: COC(=O)CC1CCC(c2ccc(-c3ccc(N)cc3)cc2)OC1]

To a mixture of (E/Z)-methyl 2-(6-(4'-nitrobiphenyl-4-yl)-2H-pyran-3(4H,5H,6H)-ylidene)acetate (70 mg, 0.20 mmol) and Pearlman's catalyst (42 mg, 0.30 mmol) was added EtOAc (1.5 ml) and MeOH (0.3 ml). The mixture was stirred under 1 atm. of hydrogen for 1 hour. The reaction mixture was filtered and washed with EtOAc, and the filtrate concentrated to afford a crude product. Column purification afforded the title compound as a white solid after drying (58 mg, 90% yield). MS (ESI) m/z 326.1 (M+1). Retention time 1.35 min. (Condition R).

Step 8. methyl 2-(6-(4'-(5-cyclobutyl-1,3,4-oxadiazol-2-ylamino)biphenyl-4-yl)tetrahydro-2H-pyran-3-yl)acetate

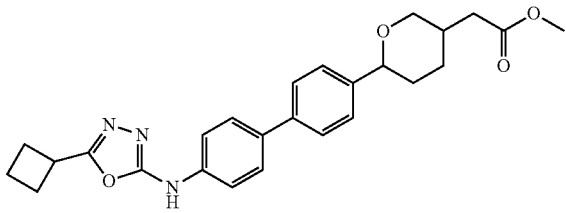 [SMILES: COC(=O)CC1CCC(c2ccc(-c3ccc(Nc4nnc(C5CCC5)o4)cc3)cc2)OC1]

To a solution of methyl 2-(6-(4'-aminobiphenyl-4-yl)tetrahydro-2H-pyran-3-yl)acetate (58 mg, 0.18 mmol) in dichloromethane (1.5 mL) was added 1,1'-thiocarbonylbis(pyridin-2(1H)-one) (45 mg, 0.19 mmol) and the reaction was let stir at room temperature for 1 hour. To the resulting bright orange reaction was added cyclobutanecarbohydrazide (30 mg, 0.27 mmol) and stirring was continued at room temperature for overnight. To the resulting mixture was added EDC (61 mg, 0.32 mmol) and stirring was continued at room temperature or 3 hr. The reaction was directly purified by column chromatography to afford the title compound as white solid after drying (43 mg, 55% yield). ESI-MS m/z: 448.1 [M+H]$^+$, retention time 1.46 min (condition R).

Step 9. Synthesis of -(6-(4'-((5-cyclobutyl-1,3,4-oxadiazol-2-yl)amino)-[1,1'-biphenyl]-4-yl)tetrahydro-2H-pyran-3-yl)acetic acid sodium salt

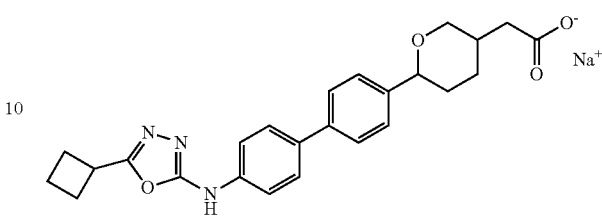

To a mixture of methyl 2-(6-(4'-(5-cyclobutyl-1,3,4-oxadiazol-2-ylamino)biphenyl-4-yl)tetrahydro-2H-pyran-3-yl) acetate (43 mg, 0.10 mmol) in THF (0.5 ml) and MeOH (0.5 ml) was added a solution of 1N NaOH (0.29 ml, 0.29 mmol). The mixture was stirred at room temperature for overnight. Afterward, the reaction mixture was concentrated to dryness afford a white solid. The solid was taken up in water to form a slurry and was subsequently filtered. The filtercake was washed with water, dried to afford the title compound (36 mg, 81% yield) as a sodium salt. The ratio of cis to trans isomer was determined to be ~1:1.2 by NMR studies. HR/MS [M+H]$^+$: found 434.2071, calc. 434.2080. RT: 1.72 (Condition L). HR/MS [M+H]$^+$: found 434.2077, calc. 434.2080. RT: 1.75 (Condition L).

The mixture was then separated by chiral SFC (OJ-H 20×250 mm, isocratic 40% MeOH+10 mM NH4OH in CO2, 75 g/min flow, 220 nM UV)) to afford a total of 4 products.

cis enantiomer 1, HR/MS [M+H]$^+$: found 434.2068, calc. 434.2080. RT: 1.77 (Condition L). $^1$H NMR (400 MHz, DMSO-d6) δ ppm 10.53 (br. s, 1H), 7.54-7.69 (m, 6H), 7.33-7.43 (m, 2H), 4.26-4.39 (m, 1H), 3.76-3.86 (m, 1H), 3.62-3.73 (m, 2H), 2.16-2.41 (m, 6H), 1.77-2.13 (m, 4H), 1.58-1.75 (m, 3H).

cis enantiomer 2, HR/MS [M+H]$^+$: found 434.2068, calc. 434.2080. RT: 2.12 (Condition L). $^1$H NMR (400 MHz, DMSO-d6) δ ppm 10.51 (br. s, 1H), 7.55-7.71 (m, 6H), 7.32-7.45 (m, 2H), 4.30-4.43 (m, 1H), 3.77-3.88 (m, 1H), 3.63-3.76 (m, 2H), 2.25-2.42 (m, 6H), 1.80-2.14 (m, 4H), 1.55-1.79 (m, 3H).

trans entantiomer 1, HR/MS [M+H]$^+$: found 434.2073, calc. 434.2080. RT: 2.27 (Condition L). $^1$H NMR (400 MHz, DMSO-d6) δ ppm 10.42 (br. s, 1H), 7.52-7.70 (m, 6H), 7.29-7.44 (m, 2H), 4.23-4.33 (m, 1H), 3.95-4.08 (m, 1H), 3.62-3.75 (m, 1H), 3.11-3.24 (m, 1H), 2.25-2.42 (m, 5H), 1.79-2.14 (m, 6H), 1.42-1.58 (m, 1H), 1.27-1.42 (m, 1H).

trans entantiomer 2, HR/MS [M+H]$^+$: found 434.2073, calc. 434.2080. RT: 2.27 (Condition L). $^1$H NMR (400 MHz, DMSO-d6) δ ppm 12.07 (br. s, 1H), 10.48 (s, 1H), 7.53-7.70 (m, 6H), 7.30-7.45 (m, 2H), 4.26-4.35 (m, 1H), 3.97-4.07 (m, 1H), 3.62-3.74 (m, 1H), 3.14-3.26 (m, 1H), 2.25-2.41 (m, 5H), 1.81-2.19 (m, 6H), 1.43-1.59 (m, 1H), 1.30-1.43 (m, 1H).

Biological Assays

The activity of compounds according to the invention can be assessed by the following inhibition assay.

DGAT1 Inhibition Assay

The enzyme preparation used in this assay is a membrane preparation from Sf9 cells overexpressing human (His)$_6$DGAT1. During all steps samples were chilled to 4° C. Sf9 cells expressing human (His)$_6$DGAT1 were thawed at room temperature and re-suspended at a 10:1 ratio (mL buffer/g of cells) in 50 mM HEPES, 1× Complete Protease Inhibitor, pH 7.5. The re-suspended pellet was homogenized for 1 min using a Brinkman PT 10/35 homogenizer with a 20 mm generator. Cells were lysed using Avestin Emulsiflex (chilled to 4° C.) at 10000-15000 psi. Lysate was centrifuged at 100,000×g for 1 h at 4° C. Supernatant was removed and pellets were re-suspended in 50 mM HEPES, 1× Complete Protease Inhibitor, pH 7.5 at ⅙ the volume of supernatant. Re-suspended pellets were pooled and homogenized with 10 strokes of a Glas-Col motor driven teflon pestle on setting 70. The protein concentration of the membrane preparation was quantified using BCA protein assay with 1% SDS. The membrane preparation was aliquoted, frozen on dry ice, and stored at −80° C.

For 50 mL, 25 mL of 0.2 M HEPES stock buffer, 0.5 mL of 1 M MgCl$_2$ (5 mM final concentration), and 24.5 mL of milli-Q H$_2$O are added to the 55 mL Wheaton Potter-Elvehjem homogenizer. Enzyme preparation (0.1 mL) is added to buffer and the mixture is homogenized with 5 strokes on ice using the Glas-Col variable speed homogenizer system on setting 70.

For 50 mL, 0.5 mL 10 mM diolein is added to 9.5 mL of EtOH in a 50 mL Falcon screw cap conical centrifuge tube. Five mL of 10 mM sodium acetate pH 4.5 is added followed by 0.5 mL of 10 mM oleoyl-CoA. Finally, the remaining 4.5 mL of 10 mM sodium acetate pH 4.5 is added followed by 30 mL of milli-Q H20. The solution should be gently agitated by hand to induce mixing. The final concentrations of EtOH and sodium acetate are 20% and 2 mM, respectively.

Dry compounds are dissolved in the appropriate volume of DMSO to a final concentration of 10 mM. A 10-point, 3-fold dose response is used to evaluate compound potency. All dilutions are performed in DMSO in a Greiner 384-well microplate.

1. 2 μL of compound in DMSO is added to the appropriate wells. 2 μL of DMSO is added to 100% activity and 100% inhibition controls.
2. 25 μL of enzyme mix is added to all wells and plate(s) are incubated for 10 min at RT.
3. 10 μL of 20% acetic acid quench is added to 100% inhibition control wells. Plate(s) are vortexed using Troemner multi-tube vortexer (setting 7 for 10 sec).
4. 25 μL of substrate mix is added to all wells. Plate(s) are vortexed using Troemner multi-tube vortexer (setting 7 for 10 sec). Plate(s) are incubated for 30 min at RT.
5. 10 μL of 20% acetic acid quench is added to all wells. Plate(s) are vortexed using Troemner multi-tube vortexer (setting 7 for 10 sec).
6. 50 μL of 1-butanol w/ glyceryl tripalmitoleate internal standard is added to all wells.
7. Plate(s) are sealed with super pierce strong plate sealer using the thermo-sealer.
8. Plate(s) are vortexed using Troemner multi-tube vortexer (setting 10 for 5 min).
9. Plate(s) are centrifuged at 162×g (1000 rpm for GH-3.8 rotor) for 5 min using Beckman GS-6R tabletop centrifuge.

Samples were analyzed by LC/MS/MS using a Waters 1525μ LC and Quattro Micro API MS. Where indicated, tripalmitolein was used as an internal standard to control for instrument variation.

HPLC Conditions:
Column: Thermo Betabasic 4, 2.1×20 mm
Solvent: 10 mM Ammonium Formate, 0.1% Formic Acid, 2% water, 98% Methanol
Isocratic run 0.5 ml per minute
Run time 1 minute Data is converted to % inhibition prior to curve fitting using the following equation:

$$\% \text{ Inhibition} = \frac{(\text{response compound} - \text{response 100\% inhibition control})}{(\text{response 100\% activity control} - \text{response 100\% inhibition control})} \times 100$$

Using the method described above, the compounds of the present invention were shown to possess inhibitory activity with IC$_{50}$ values ranging from 0.001 μM to 100 μM.

Cellular Assay to Measure Activity of DGAT1 Inhibitors in Mammalian Cells.

C2C12 cells are an immortal mouse skeletal muscle cell line showing an 8-fold enrichment for M DGAT1 versus DGAT2. C2C12 cells were routinely cultured in 150 cm2 flasks with DMEM (25 mM glucose) containing 10% FBS, 4 mM L-glutamine, 100 U/ml penicillin and 100 μg/ml streptomycin (30 ml per flask), at 37° C., 5% CO2 and 95% humidity. All studies were performed on cells at passage 10 or less.

C2C12 cells were seeded in 96-well plates in DMEM containing 4.5 mM glucose and 10% FBS, 18 h (at 37° C.) prior to assay (all wells of the plate are used). Following 18 h incubation, seeding medium was then replaced with DMEM (5 mM glucose) containing 250 μM oleate (complexed to BSA) and compounds or DMSO, for 2 h (at 37° C.). Compounds were added at 1:3 dilution, 11 points and DMSO control, the starting concentration was usually 40 μM. Each point was dosed in quadruplicate allowing 2 compounds to be dosed per plate. The medium was removed at the end of the incubation and 200 μl/well of 1-butanol added. The 1-butanol contained an internal standard, tripalmitolein (2 μM). The plates were sealed with an adhesive plate sealer and left at room temperature for at least 30 min, then spun down at 209×g for 5 min.

Butanolic extracts were transferred to 384-well LC-MS plates (80 μl/well) and the plate heatsealed with a foil plate sealer. The 384-well plates containing sample were spun down at 209×g for 5 min prior to loading on the LC-MS.

Samples were analyzed by LC/MS using a Waters 1525μ LC and Quattro Micro API MS.

Where indicated, tripalmitolein was used as an internal standard to control for instrument variation. HPLC conditions as above.

Table 1 below shows the inhibitory activity (IC$_{50}$ values) of representative compounds to human DGAT1.

TABLE 1

Activities of compounds of the invention in the DGAT1 assay

| Example | Name | DGAT1 IC$_{50}$ (μM) | DGAT1-C2C12 IC$_{50}$ (μM) |
|---|---|---|---|
| 1 | 2-(5-(4'-(2-methyl-5-(trifluoromethyl)oxazole-4-carboxamido)-[1,1'-biphenyl]-4-yl)tetrahydro-2H-pyran-2-yl)acetic acid, racemate | 1.4 | 0.066 |
| 2 | 2-(5-(4'-(2-methyl-5-(trifluoromethyl)oxazole-4-carboxamido)-[1,1'-biphenyl]-4- | 5.9 | 2.2 |

TABLE 1-continued

Activities of compounds of the invention in the DGAT1 assay

| Example | Name | DGAT1 IC$_{50}$ (μM) | DGAT1-C2C12 IC$_{50}$ (μM) |
|---|---|---|---|
| | yl)tetrahydro-2H-pyran-2-yl)acetic acid, cis enantiomer 1 | | |
| 3 | 2-(5-(4'-(2-methyl-5-(trifluoromethyl)oxazole-4-carboxamido)-[1,1'-biphenyl]-4-yl)tetrahydro-2H-pyran-2-yl)acetic acid, trans enantiomer 1 | 0.82 | 0.01 |
| 4 | 2-(5-(4'-(2-methyl-5-(trifluoromethyl)oxazole-4-carboxamido)-[1,1'-biphenyl]-4-yl)tetrahydro-2H-pyran-2-yl)acetic acid, trans enantiomer 2 | 0.3 | 0.017 |
| 5 | 2-(5-(4'-(2-methyl-5-(trifluoromethyl)oxazole-4-carboxamido)-[1,1'-biphenyl]-4-yl)tetrahydro-2H-pyran-2-yl)acetic acid, cis enantiomer 2 | 2.6 | 0.33 |
| 6 | 2-(5-(4'-((5-cyclobutyl-1,3,4-oxadiazol-2-yl)amino)-[1,1'-biphenyl]-4-yl)tetrahydro-2H-pyran-2-yl)acetic acid, racemate | 0.31 | 0.1 |
| 7 | 2-(6-(4'-((5-cyclobutyl-1,3,4-oxadiazol-2-yl)amino)-[1,1'-biphenyl]-4-yl)tetrahydro-2H-pyran-3-yl)acetic acid sodium salt, racemate | 0.1 | N/A |
| 8 | 2-(6-(4'-((5-cyclobutyl-1,3,4-oxadiazol-2-yl)amino)-[1,1'-biphenyl]-4-yl)tetrahydro-2H-pyran-3-yl)acetic acid sodium salt, cis enantiomer 1 | 0.76 | N/A |
| 9 | 2-(6-(4'-((5-cyclobutyl-1,3,4-oxadiazol-2-yl)amino)-[1,1'-biphenyl]-4-yl)tetrahydro-2H-pyran-3-yl)acetic acid sodium salt, trans enantiomer 1 | 0.13 | N/A |
| 10 | 2-(6-(4'-((5-cyclobutyl-1,3,4-oxadiazol-2-yl)amino)-[1,1'-biphenyl]-4-yl)tetrahydro-2H-pyran-3-yl)acetic acid sodium salt, cis enantiomer 2 | 0.57 | N/A |
| 11 | 2-(6-(4'-((5-cyclobutyl-1,3,4-oxadiazol-2-yl)amino)-[1,1'-biphenyl]-4-yl)tetrahydro-2H-pyran-3-yl)acetic acid sodium salt, trans enantiomer 2 | 1.2 | N/A |

CONCLUSIONS

It can be seen that the compounds of the invention are useful as inhibitors of DGAT1 and therefore useful in the treatment of diseases and conditions mediated by DGAT1 such as the metabolic disorders disclosed herein.

It will be understood that the invention has been described by way of example only and modifications may be made whilst remaining within the scope and spirit of the invention.

We claim:

1. A compound according to formula (I) or a salt or solvate thereof:

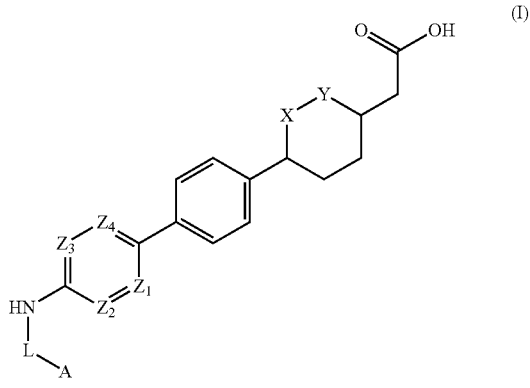

wherein
X is O or CH$_2$;
Y is O or CH$_2$; wherein one of X and Y is O and the other is CH$_2$;
Z$_1$, Z$_2$, Z$_3$ and Z$_4$ are each, independently, N or CH;
L is C(O) or absent; and
A is a substituted oxazole, thiazole, oxadiazole or thiadiazole substituted with at least one C$_{1-6}$alkyl, C$_{3-7}$cycloalkyl or C$_{1-6}$haloalkyl.

2. The compound according to claim 1, wherein the compound is of formula (II) or a salt or solvate thereof:

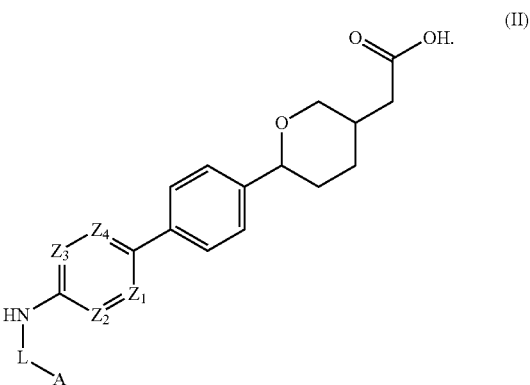

3. The compound according to claim 1, wherein the compound is of formula (III) or a salt or solvate thereof:

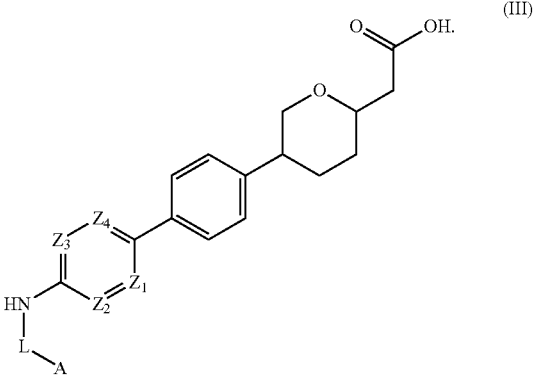

4. The compound according to claim 1 or a salt or solvate thereof, wherein Z$_1$, Z$_2$, Z$_3$ and Z$_4$ are all CH.

5. The compound according to claim 1 or a salt or solvate thereof, wherein $Z_1$ is N and $Z_2$, $Z_3$ and $Z_4$ are each CH.

6. The compound according to claim 1 or a salt or solvate thereof, wherein $Z_2$ is N and $Z_1$, $Z_3$ and $Z_4$ are each CH.

7. The compound according to claim 1 or a salt or solvate thereof, wherein $Z_1$ and $Z_2$ are both N and $Z_3$ and $Z_4$ are both CH.

8. The compound according to claim 1 or a salt or solvate thereof, wherein L is C(O).

9. The compound according to claim 1 or a salt or solvate thereof, wherein L is absent.

10. The compound according to claim 1 or a salt or solvate thereof, wherein A is selected from:

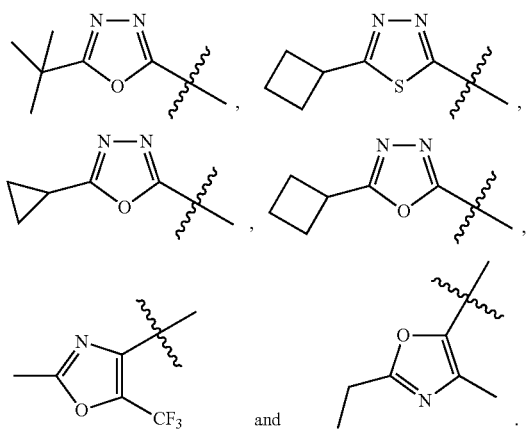

11. The compound according to claim 1 or a salt or solvate thereof, wherein A is selected from:

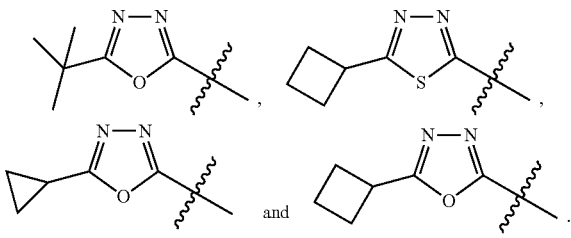

12. The compound according to claim 1 or a salt or solvate thereof, wherein A is selected from

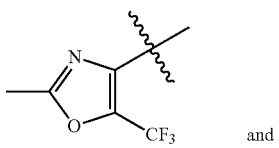

and

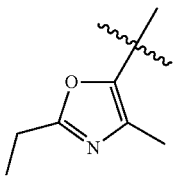

13. The compound of claim 1 or a salt or solvate thereof, wherein the compound is selected from:
- 2-(5-(4'-(2-methyl-5-(trifluoromethyl)oxazole-4-carboxamido)-[1,1'-biphenyl]-4-yl)tetrahydro-2H-pyran-2-yl)acetic acid;
- 2-(5-(4'-(2-methyl-5-(trifluoromethyl)oxazole-4-carboxamido)-[1,1'-biphenyl]-4-yl)tetrahydro-2H-pyran-2-yl)acetic acid, cis enantiomer 1;
- 2-(5-(4'-(2-methyl-5-(trifluoromethyl)oxazole-4-carboxamido)-[1,1'-biphenyl]-4-yl)tetrahydro-2H-pyran-2-yl)acetic acid, trans enantiomer 1;
- 2-(5-(4'-(2-methyl-5-(trifluoromethyl)oxazole-4-carboxamido)-[1,1'-biphenyl]-4-yl)tetrahydro-2H-pyran-2-yl)acetic acid, trans enantiomer 2;
- 2-(5-(4'-(2-methyl-5-(trifluoromethyl)oxazole-4-carboxamido)-[1,1'-biphenyl]-4-yl)tetrahydro-2H-pyran-2-yl)acetic acid, cis enantiomer 2;
- 2-(5-(4'-((5-cyclobutyl-1,3,4-oxadiazol-2-yl)amino)-[1,1'-biphenyl]-4-yl)tetrahydro-2H-pyran-2-yl)acetic acid, racemate;
- 2-(6-(4'-((5-cyclobutyl-1,3,4-oxadiazol-2-yl)amino)-[1,1'-biphenyl]-4-yl)tetrahydro-2H-pyran-3-yl)acetic acid sodium salt, racemate;
- 2-(6-(4'-((5-cyclobutyl-1,3,4-oxadiazol-2-yl)amino)-[1,1'-biphenyl]-4-yl)tetrahydro-2H-pyran-3-yl)acetic acid sodium salt, cis enantiomer 1;
- 2-(6-(4'-((5-cyclobutyl-1,3,4-oxadiazol-2-yl)amino)-[1,1'-biphenyl]-4-yl)tetrahydro-2H-pyran-3-yl)acetic acid sodium salt, trans enantiomer 1;
- 2-(6-(4'-((5-cyclobutyl-1,3,4-oxadiazol-2-yl)amino)-[1,1'-biphenyl]-4-yl)tetrahydro-2H-pyran-3-yl)acetic acid sodium salt, cis enantiomer 2;
- 2-(6-(4'-((5-cyclobutyl-1,3,4-oxadiazol-2-yl)amino)-[1,1'-biphenyl]-4-yl)tetrahydro-2H-pyran-3-yl)acetic acid sodium salt, trans enantiomer 2; and a salt or solvate thereof.

14. A pharmaceutical composition comprising one or more pharmaceutically acceptable carriers and a therapeutically effective amount of a compound of claim 1.

15. A pharmaceutical combination comprising a therapeutically effective amount of the compound according to claim 1 and a second therapeutically active agent.

16. A method for the treatment of a disease or condition mediated by DGAT1 activity in a subject having said disease or condition, wherein the method comprises administering to the subject a therapeutically effective amount of the compound according to claim 1, wherein the disease or condition is selected from the group consisting of impaired glucose tolerance, Type II diabetes and obesity.

17. A method of treating impaired glucose tolerance, Type II diabetes or obesity comprising administering to a subject having impaired glucose tolerance, Type II diabetes or obesity an effective amount of a composition comprising a compound of claim 1.

* * * * *